(12) United States Patent
Estes

(10) Patent No.: US 8,221,385 B2
(45) Date of Patent: *Jul. 17, 2012

(54) INFUSION PUMP SYSTEMS AND METHODS

(75) Inventor: Mark C. Estes, Malibu, CA (US)

(73) Assignee: Asante Solutions, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/071,061

(22) Filed: Mar. 24, 2011

(65) Prior Publication Data
US 2011/0172635 A1    Jul. 14, 2011

Related U.S. Application Data

(62) Division of application No. 12/195,034, filed on Aug. 20, 2008, now Pat. No. 7,959,598.

(51) Int. Cl.
*A61M 31/00* (2006.01)
*A61M 37/00* (2006.01)
*A61M 1/00* (2006.01)

(52) U.S. Cl. ........ 604/504; 604/500; 604/503; 604/507; 604/65; 604/67; 604/131; 604/31

(58) Field of Classification Search .............. 604/65–67, 604/500, 503, 504, 522, 507, 31
See application file for complete search history.

(56) References Cited

U.S. PATENT DOCUMENTS

| 5,984,894 | A | 11/1999 | Poulsen et al. |
|---|---|---|---|
| 6,551,276 | B1 | 4/2003 | Mann et al. |
| 6,554,798 | B1 | 4/2003 | Mann et al. |
| 6,659,978 | B1 | 12/2003 | Kasuga |
| 6,691,043 | B2 | 2/2004 | Ribeiro, Jr. |
| 6,744,350 | B2 | 6/2004 | Blomquist |
| 6,852,104 | B2 | 2/2005 | Blomquist |
| 6,925,393 | B1 | 8/2005 | Kalatz et al. |
| 6,936,029 | B2 | 8/2005 | Mann et al. |
| 6,979,326 | B2 | 12/2005 | Mann et al. |
| 6,997,920 | B2 | 2/2006 | Mann et al. |
| 7,025,743 | B2 | 4/2006 | Mann et al. |
| 7,109,878 | B2 | 9/2006 | Mann et al. |
| 7,278,983 | B2 | 10/2007 | Ireland et al. |

(Continued)

FOREIGN PATENT DOCUMENTS
EP    0-062-974    10/1982
(Continued)

OTHER PUBLICATIONS

"Which Insulin Pump is Right for Me?", Albany Medical Center, Goodman Diabetes Service, Jan. 2006, 4 pages.

(Continued)

*Primary Examiner* — Kevin C Sirmons
*Assistant Examiner* — Bradley Thomas, Jr.
(74) *Attorney, Agent, or Firm* — Fish & Richardson P.C.

(57) ABSTRACT

Some embodiments an infusion pump system can be used to determine a user's total insulin load (TIL) that provides an accurate indication of the insulin previously delivered to the user's body which has not yet acted. In particular embodiments, the TIL can account for both the bolus deliveries and the basal deliveries that have occurred over a period of time. Such information may be useful, for example, when the infusion pump is operated in conjunction with a continuous glucose monitoring device.

20 Claims, 14 Drawing Sheets

U.S. PATENT DOCUMENTS

| | | | |
|---|---|---|---|
| 7,959,598 B2 * | 6/2011 | Estes | 604/65 |
| 2004/0167464 A1 | 8/2004 | Ireland et al. | |
| 2004/0176720 A1 | 9/2004 | Kipfer | |
| 2007/0073228 A1 | 3/2007 | Mernoe et al. | |
| 2007/0073235 A1 | 3/2007 | Estes et al. | |
| 2007/0073236 A1 | 3/2007 | Mernoe et al. | |
| 2007/0118405 A1 | 5/2007 | Campbell et al. | |
| 2007/0167912 A1 | 7/2007 | Causey et al. | |
| 2007/0173761 A1 | 7/2007 | Kanderian, Jr. et al. | |
| 2007/0179444 A1 | 8/2007 | Causey et al. | |
| 2008/0125700 A1 | 5/2008 | Moberg et al. | |
| 2008/0294094 A1 | 11/2008 | Mhatre et al. | |
| 2008/0294142 A1 | 11/2008 | Patel et al. | |

FOREIGN PATENT DOCUMENTS

| | | |
|---|---|---|
| EP | 0-275-213 | 7/1988 |
| EP | 1-045-146 | 12/2000 |
| EP | 1 818 664 | 8/2007 |
| WO | WO 2004/056412 | 7/2004 |
| WO | WO 2004/110526 | 12/2004 |

OTHER PUBLICATIONS

"Using the Deltec Cozmo Insulin Pump Correction Bolus Feature" believed to be publicly available before May 5, 2008, pp. 36-41.

* cited by examiner

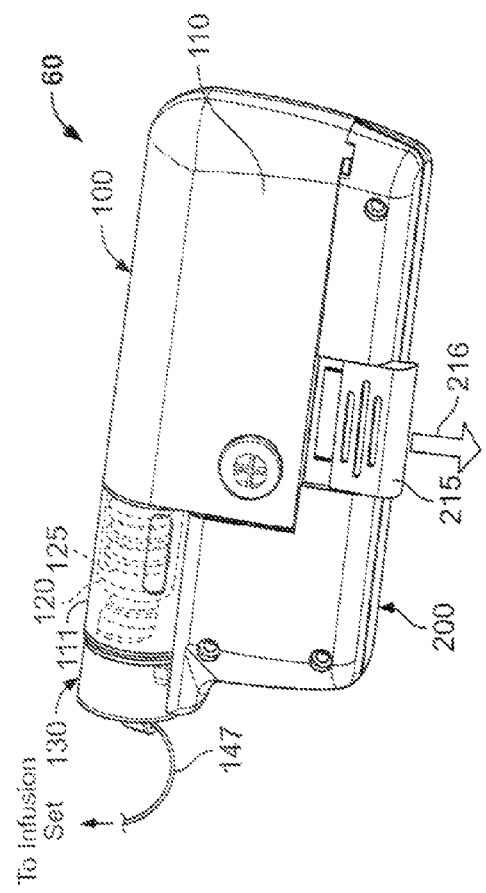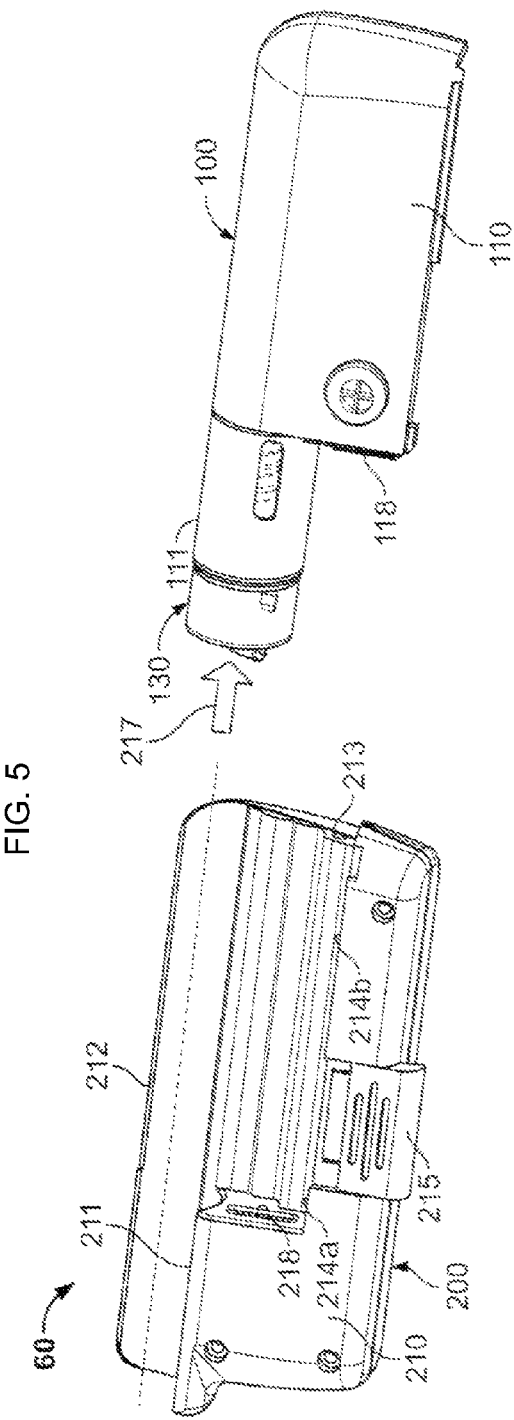
FIG. 5
FIG. 6

INFUSION PUMP SYSTEMS AND METHODS

CROSS-REFERENCE TO RELATED APPLICATION(S)

This is a divisional of U.S. application Ser. No. 12/195,034 filed on Aug. 20, 2008, the entire contents of which are expressly incorporated herein by reference.

TECHNICAL FIELD

This disclosure relates to portable infusion pump systems to deliver fluids, such as insulin infusion pump systems or the like.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels. In some circumstances, the dosage of medicine delivered by the infusion pump acts within the patient's body over a long period of time. Such conditions, for example, may cause a patient to have an amount of non-activated insulin in his or her system even thought the infusion pump is programmed to deliver the next dosage in a series of insulin dosages.

SUMMARY

Some embodiments an infusion pump system can be used to determine a user's total insulin load (TIL) that provides an accurate indication of the insulin already delivered to the user's body which has not yet acted. In particular embodiments, the TIL can account for both the bolus deliveries and the basal deliveries that have occurred over a period of time. Such information can be valuable to a user when the infusion pump is operated in conjunction with a glucose monitoring device worn by the user. Moreover, the TIL information can be readily displayed to the user as a quick reference of his or her status. For example, the infusion pump system can include a user interface that contemporaneously displays the user's blood glucose value and the total insulin load, thereby enabling the user to make informed decisions regarding the current and future status of his or her blood glucose level.

In particular embodiments, a medical infusion pump system may include a portable pump housing that receives insulin for dispensation to a user. The pump housing may at least partially contain a pump drive system to dispense the insulin through a flow path to the user. The pump system also may include a controller that activates the pump drive system to dispense the insulin from the portable pump housing. The pump system may further include a monitoring device that communicates glucose information to the controller. The glucose information may be indicative of a blood glucose level of the user. The pump system also may include a user interface coupled to the controller including a display device that contemporaneously displays a glucose value indicative of the blood glucose level of the user and a total insulin load indicative of bolus and basal insulin dosages that have dispensed but not yet acted in the user.

Some embodiments of a method of operating an insulin infusion pump system may include determining a total insulin load for a particular time that accounts for a bolus insulin load, a basal insulin load, and a previous food component. The bolus insulin load may be indicative of one or more bolus insulin dosages that have been dispensed into a user from a portable infusion pump system but not yet acted in the user. The basal insulin load may be indicative of one or more basal insulin dosages that have been dispensed into the user from the portable infusion pump system but not yet acted in the user. The previous food component may be based upon previous food intake that has not yet metabolized in the user. The method also may include storing a calculated value for the total insulin load and a time value for the particular time in a computer-readable memory device of the portable infusion pump system. The method may further include displaying the calculated value for the total insulin load on a display device of the portable infusion pump system.

In certain embodiments, a method of operating an insulin infusion pump system may include receiving user input indicative of a request to suggest a bolus dosage. The method may also include receiving user input indicative of a proposed food intake to be consumed by a user of a portable infusion pump system. The method may further include receiving glucose information indicative of a glucose level of the user. Also, the method may include determining a bolus suggestion value according to a function that includes a total insulin load of the user. The total insulin load may account for (i) a bolus insulin load indicative of one or more bolus insulin dosages that have been dispensed into the user but not yet acted in the user, (ii) a basal insulin load indicative of one or more basal insulin dosages that have been dispensed into the user from the portable infusion pump system but not yet acted in the user; and (iii) a previous food component based upon previous food intake that has not yet metabolized in the user. The method may also include displaying the bolus suggestion value on a display device of the portable infusion pump system.

These and other embodiments described herein may provide one or more of the following advantages. First, the infusion pump system can be used to provide a TIL value that accurately estimates the amount of previously delivered insulin that has not yet acted in the user's body. For example, the TIL can be determined in a manner that accounts for both the bolus deliveries and the basal deliveries (not merely previous bolus deliveries). As such, the TIL values may accurately reflect basal rate changes and the impact of stopping insulin delivery or changing basal delivery for a short period of time (e.g., a temporary basal rate change). Also, in particular embodiments, the TIL can account for the user's previously consumed food in addition to the bolus deliveries and the basal deliveries. In these circumstances, the TIL values may accurately reflect both the previously dispensed insulin that has not yet acted and the previously consumed food that has not yet been metabolized. Second, the TIL information provided by the infusion pump system can provide the user with opportunities for informed decision-making when the infusion pump is operated in conjunction with a continuous glucose monitoring device. For example, the infusion pump system can include a user interface that contemporaneously displays the user's blood glucose value and the total insulin load, thereby enabling the user to make informed decisions regarding the current and future status of his or her blood glucose level. Third, the infusion pump system can include a bolus suggestion feature that accounts for the user's TIL when suggesting a new bolus of insulin prior to a meal of other food intake. For example, in response to a user's request, the infusion pump system may communicate a suggested bolus dosage of insulin that is calculated to account for the meal of other food to be consumed (e.g., a food bolus), the current difference between the user's actual blood glucose level and the targeted blood glucose level (e.g., a correction bolus), and the amount of previous basal and bolus insulin that has not yet acted in the user's body (e.g., a TIL factor).

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 5-6 are perspective views of a pump device being detached from a controller device of the system of FIG. 1, in accordance with some embodiments.

Like reference symbols in the various drawings indicate like elements.

DETAILED DESCRIPTION

Figure 1:
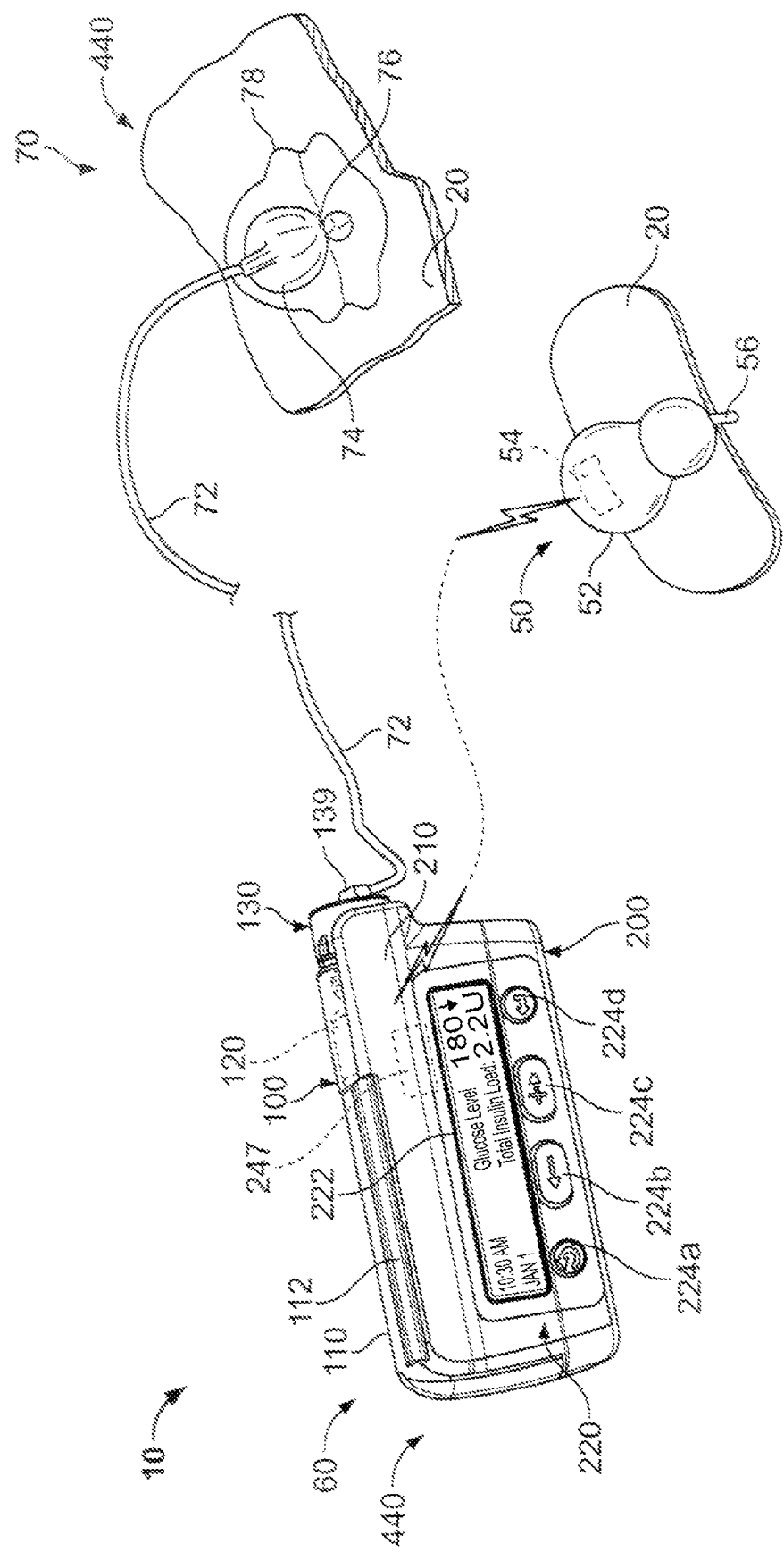
FIG. 1 is a perspective view of an infusion pump system in accordance with some embodiments.

Referring to FIG. 1, an infusion pump system 10 can include a pump assembly 60 used to supply insulin or other medication to a user via, for example, an infusion set 70. In some embodiments, a glucose monitoring device 50 can be in communication with the infusion pump assembly 60 for the purpose of supplying data indicative of a user's blood glucose level to a controller device 200 included in the pump assembly 60. The infusion pump system 10 can be configured to supply a substantially continuous basal rate of insulin (or other medication) with user-selected bolus dosages. The basal rate can be selected to maintain a user's blood glucose level in a target range during normal activity when the user is not eating or otherwise consuming food items, and the selected bolus deliveries may provide substantially larger amounts of insulin to limit the blood glucose level during certain circumstances, such as the consumption of carbohydrates and other food items. The basal and bolus insulin dispensed into the user's system may act over a period of time to control the user's blood glucose level. As such, the user's body may include some amount of insulin that has not yet acted even while the infusion pump assembly 60 is activated to deliver additional dosages (basal, bolus, or both). In these circumstances, the infusion pump assembly 60 can be used to determine a user's total insulin load (TIL) that provides an accurate indication of the insulin which has not yet acted in the user's body. For example, as shown in FIG. 1, the controller device 200 of the infusion pump assembly 60 can include a user interface 220 configured to calculate and display the TIL value along with the user's blood glucose value, thereby enabling the user to make informed decisions regarding the current and future status of his or her blood glucose level.

The TIL information provided by the controller device 200 can be determined in a manner that accounts for both the bolus deliveries and the basal deliveries (not merely bolus deliveries alone). As described in more detail below, this process for determining the TIL value can accurately reflect basal rate changes and the effects from stopping insulin delivery or changing basal delivery for a short period of time (e.g., a temporary basal rate change). Also, in further embodiments, the TIL information provided by the controller device 200 can be determined in a manner that accounts for the user's previously consumed food (along with the previous basal and bolus deliveries). As described in more detail below, such a process for determining the TIL value can reveal the effects from both the previously dispensed insulin that has not yet acted and the previously consumed food that has not yet been metabolized. In some embodiments, data related to the TIL, such as total insulin load values and the times at which they were calculated, can be stored in a memory device (described below) of the controller device 200. This data can be used, for example, by the controller device 200 in a process to suggest a new bolus dosage based in response a user's request. For example, the bolus suggestion value can be based, at least in part, on a user's current blood glucose level, food information supplied by the user (e.g., proposed food intake), and a recently calculated TIL value for the user. Moreover, the TIL data stored in the memory device of the controller 200 can be exported to an external computer system for analysis by a physician, the user, or both. For example, as described in more detail below, the TIL data can be presented in a plot format to assist the user and physician in making adjustments to the user's insulin delivery patterns or food intake to improve management the user's blood glucose level.

Still referring to FIG. 1, the glucose monitoring device 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of characteristics of the user's blood (e.g., the user's blood glucose level or the like). In response to the measurements made by the sensor shaft 56, the glucose monitoring device 50 can employ the wireless communication device 54 to transmit data to the controller device 200 of the pump assembly 60.

In some embodiments, the monitoring device 50 may include a circuit that permits sensor signals (e.g., data from the sensor shaft 56) to be communicated to the communication device 54. The communication device 54 can transfer the collected data to the infusion pump assembly 60 (e.g., by wireless communication to a communication device 247 arranged in the pump assembly 60). In some embodiments, the monitoring device 50 can employ other methods of obtaining information indicative of a user's blood characteristics and transferring that information to the infusion pump assembly 60. For example, an alternative monitoring device may employ a micropore system in which a laser porator creates tiny holes in the uppermost layer of a user's skin, through which interstitial glucose is measured using a patch. Alternatively, the monitoring device can use iontophoretic methods to non-invasively extract interstitial glucose for measurement. In other examples, the monitoring device can include non-invasive detection systems that employ near IR, ultrasound or spectroscopy, and particular embodiments of glucose-sensing contact lenses. Invasive methods involving optical means of measuring glucose could also be added. In yet another example, the monitoring device can include an optical detection instrument that is inserted through the skin for measuring the user's glucose level.

Furthermore, it should be understood that in some embodiments, the monitoring device 50 can be in communication with the pump assembly 60 via a wired connection. In other embodiments of the pump system 10, test strips (e.g., blood test strips) containing a sample of the user's blood can be inserted into a strip reader portion of the pump assembly 60 to be tested for characteristics of the user's blood. Alternatively, the test strips (e.g., glucose test strips) containing a sample of the user's blood can be inserted into a glucose meter device (not shown in FIG. 1), which then analyzes the characteristics of the user's blood and communicates the information (via a wired or wireless connection) to the pump assembly 60. In still other embodiments, characteristics of the user's blood glucose information can be entered directly into the pump system 10 via a user interface on the controller device 200.

Figure 2:
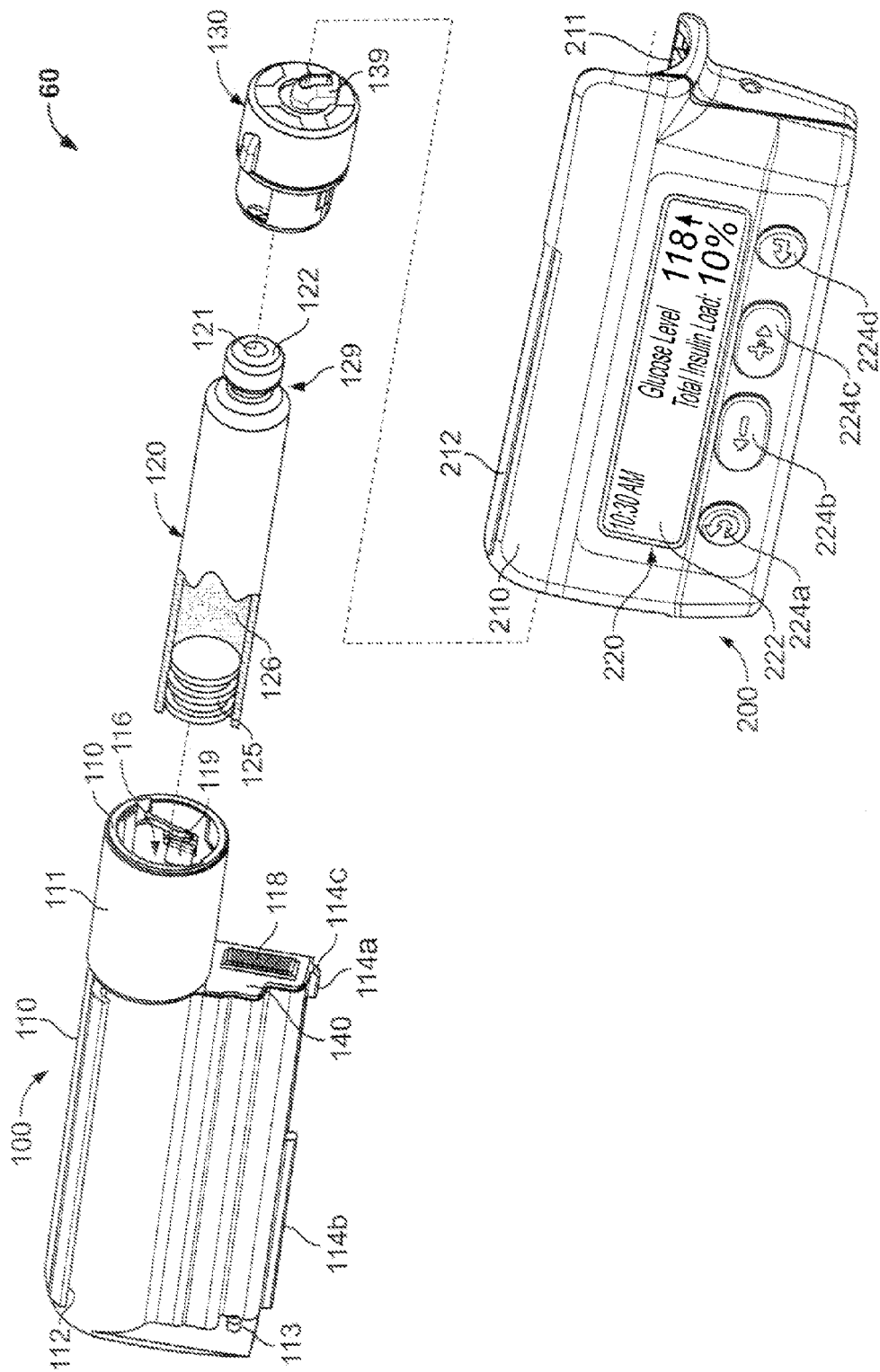
FIG. 2 is a perspective exploded view of an infusion pump assembly of the system of FIG. 1.

Referring now to FIGS. 1-2, the infusion pump assembly 60 can include a pump device 100 and the controller device 200 that communicates with the pump device 100. The pump device 100 includes a housing structure 110 that defines a cavity 116 in which a fluid cartridge 120 can be received. The pump device 100 also includes a cap device 130 to retain the fluid cartridge 120 in the cavity 116 of the housing structure 110. The pump device 100 includes a drive system (described in more detail below in connection with FIG. 10) that advances a plunger 125 in the fluid cartridge 120 so as to dispense fluid therefrom. In some embodiments, the dispensed fluid exits the fluid cartridge 120, passes through a flexible tube 72 of the infusion set 70 to a cannula housing 74. The dispensed fluid can enter through the skin via a cannula 76 attached to the underside of the cannula housing 74.

In some embodiments, the controller device 200 communicates with the pump device 100 to control the operation of the pump drive system. When the controller device 200, the pump device 100 (including the cap device 130 in this embodiment), and the fluid cartridge 120 are assembled together, the user may conveniently wear the infusion pump assembly 60 on the user's skin under clothing or in the user's pocket while receiving the fluid dispensed from the pump device 100 (refer, for example, to FIGS. 3-4). Thus, in some embodiments, the pump assembly can operate as a portable unit that provides reliable delivery of insulin or another medication in a discrete manner.

As described in more detail below, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device 100 to the reusable controller device 200 for the dispensation of fluid from a new fluid cartridge 120. Accordingly, the user is permitted to reuse the controller device 200 (which may include complex or valuable electronics) while disposing of the relatively low-cost pump device 100 after each use. Such a pump assembly 60 can provide enhanced user safety as a new pump device 100 (and drive system therein) is employed with each new fluid cartridge 120.

Briefly, in use, the pump device 100 can be configured to removably attach to the controller device 200 in a manner that provides a secure fitting, an overall compact size, and a reliable electrical connection. The compact size permits the infusion pump assembly 60 to be discrete and portable. As described in more detail below, the controller device 200 of the infusion pump system can be used to provide TIL information that accurately estimates the amount of previously delivered insulin that has not yet acted in the user's body. In these embodiments, the TIL information can provide the user with opportunities for informed decision-making when the pump assembly 60 is operated in conjunction with the monitoring device 50. In addition, the controller device 200 can provide a bolus suggestion feature that accounts for the user's TIL when suggesting a new bolus of insulin prior to a meal of other food intake. Because the bolus suggestion feature accounts for the amount of previous basal and bolus insulin that has not yet acted in the user's body, the controller device 200 can provide a suitable bolus suggestion amount that generally avoids excessive stacking of insulin doses.

It should be understood that, in alternative embodiments, the pump device 100 and the controller device 200 can be configured as a single unit in which the control components and the pump drive system are arranged in a single housing. In these alternative embodiments, the pump assembly (including the controller device and the pump device) may have a different size and shape and may operate as a reusable unit that can communicate with a number of monitoring devices 50 over a period of time.

Referring again to FIGS. 1-2, in some embodiments, the pump system 10 is a medical infusion pump system that is configured to controllably dispense a medicine from the cartridge 120. As such, the fluid cartridge 120 may contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines. The medicine dispensed from the cartridge 120 into the user's system may act over a period of time in the user's body. As such, the user's body may include some amount of medicine that has not yet acted even while the infusion pump assembly 60 is activated to deliver additional dosages of the medicine (basal, bolus, or both). The infusion pump assembly 60 can be used to determine a user's total medicine load that provides an accurate indication of the medicine which has not yet acted in the user's body. The total medicine load can be determine by the controller device 200 in a manner that accounts for both the bolus deliveries and the basal deliveries of the medicine (similar to the process for determining the total insulin load as described below). It should be understood from the description herein that the fluid cartridge 120 may have a configuration other than that depicted in FIG. 2. For example, the fluid cartridge may have a different outer shape or a different reservoir volume. In another example, the fluid cartridge may comprise a reservoir that is integral with the pump housing structure 110 (e.g., the fluid cartridge can be defined by one or more walls of the pump housing structure 110 that surround a plunger to define a reservoir in which the medicine is injected or otherwise received).

In some embodiments, the pump device 100 may include one or more structures that interfere with the removal of the medicine cartridge 120 after the medicine cartridge 120 is inserted into the cavity 116. For example, as shown in FIG. 2, the pump housing structure 110 may include one or more retainer wings 119 that at least partially extend into the cavity 116 to engage a portion of the medicine cartridge 120 when the medicine cartridge 120 is installed therein. In this embodiment, the pump housing structure 110 includes a pair of opposing retainer wings 119 (only one is shown in the view in FIG. 2) that flex toward the inner surface of the cavity 116 during insertion of the medicine cartridge 120. After the medicine cartridge is inserted to a particular depth, the retainer wings 119 are biased to flex outward (toward the center of the cavity 116) so that the retainer wings 119 engage a neck portion 129 of the medicine cartridge 120. This engagement with the retainer wings 119 and the neck portion 129 hinder any attempts to remove the medicine cartridge 120 away from the pump device 100. Alternative embodiments can include other features and/or configurations to hinder the removal of the medicine cartridge 120.

Embodiments of the pump device 100 that hinder the removal of the medicine cartridge 120 may facilitate the "one-time-use" feature of the pump device 100. Because the retainer wings 119 can interfere with attempts to remove the medicine cartridge 120 from the pump device 100, the pump device 100 will be discarded along with the medicine cartridge 120 after the medicine cartridge 120 is emptied, expired, or otherwise exhausted. The retainer wings 119 may serve to hinder attempts to remove the exhausted medicine cartridge 120 and to insert a new medicine cartridge 120 into the previously used pump device 100. Accordingly, the pump device 100 may operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 1-2, the cap device 130 can be joined with the pump device 100 after the medicine cartridge is inserted in the cavity 116. It should be understood that the cap device 130 may supplement or replace the previously described retainer wings 119 by locking into position after joining with the pump housing 110, thereby hindering removal of the fluid cartridge 120 in the pump housing 110. As shown in FIGS. 1-2, the cap device 130 may include an output port 139 that connects with the tubing 72 for dispensation of the medicine to the user. In some embodiments, the output port 139 may have an angled orientation such that a portion of the tubing extends transversely to the central axis of the cartridge 120 and cap device 130. The output port 139 can be configured to mate with tubing 72 of the infusion set 70 (FIG. 1).

In some embodiments, the controller device 200 may be removably attached to the pump device 100 so that the two components are mechanically mounted to one another in a fixed relationship. Such a mechanical mounting can form an electrical connection between the removable controller device 200 and the pump device 100. For example, the controller device 200 may be in electrical communication with a portion of a drive system (described in connection with FIG. 10) of the pump device 100. As described in more detail below, the pump device 100 includes a drive system that causes controlled dispensation of the medicine or other fluid from the cartridge 120. In some embodiments, the drive system incrementally advances a piston rod longitudinally into the cartridge 120 so that the fluid is forced out of an output end 122. The septum 121 at the output end 122 of the fluid cartridge 120 can be pierced to permit fluid outflow when the cap device 130 is connected to the pump housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

The controller device 200 may be configured to removably attach to the pump device 100, for example, in a side-by-side arrangement. The compact size permits the infusion pump assembly 60 to be discrete and portable when the pump device 100 is attached with the controller device 200 (as shown in FIG. 1). In this embodiment, the controller device 200 includes a controller housing structure 210 having a number of features that are configured to mate with complementary features of the pump housing structure 110 so as to form a releasable mechanical connection (described below in more detail in connection with FIGS. 5-7). Such mating features of the pump housing structure 110 and the controller housing structure 210 can provide a secure connection when the controller device 200 is attached to the pump device 100

As shown in FIG. 2, the pump device 100 may include an electrical connector 118 (e.g., having conductive pads, pins, or the like) that are exposed to the controller device 200 and that mate with a complementary electrical connector (refer to connector 218 in FIG. 6) on the adjacent face of the controller device 200. The electrical connectors 118 and 218 provide the electrical communication between the control circuitry (refer, for example, to FIG. 9) housed in the controller device 200 and at least a portion of the drive system or other components of the pump device 100. In some exemplary embodiments, the electrical connectors 118 and 218 permit the transmission of electrical control signals to the pump device 100 and the reception of feedback signals (e.g., sensor signals) from particular components within the pump device 100. Furthermore, as described in more detail below, the infusion pump assembly 60 may include a gasket 140 that provides a seal which is resistant to migration of external contaminants when the pump device 100 is attached to the controller device 200. Thus, in some embodiments, the pump device 100 and the controller device 200 can be assembled into a water resistant configuration that protects the electrical interconnection from water migration (e.g., if the user encounters water while carrying the pump assembly 60).

Referring again to FIGS. 1-2, the controller device 200 includes the user interface 220 that permits a user to monitor the operation of the pump device 100. In some embodiments, the user interface 220 includes a display 222 and one or more user-selectable buttons (e.g., four buttons 224a, 224b, 224c, and 224d in this embodiment). The display 222 may include an active area in which numerals, text, symbols, images, or a combination thereof can be displayed (refer, for example, to FIG. 2). For example, the display 222 may be used to communicate a number of status indicators, alarms, settings, and/or menu options for the infusion pump system 10. In some embodiments, the display 222 can indicate the user's blood glucose level, an indication that the user's blood glucose level is rising or falling, and the TIL information. In the example depicted in FIG. 1, the TIL information shown in the display 222 is "2.2 U", which indicates that approximately 2.2 units of dispensed insulin (including previous basal and bolus dosages) has yet to act on the user's blood glucose level (in particular embodiments, after accounting for any previously consumed food that has not yet been metabolized). In this embodiment, the display 222 also indicates that the user's blood glucose level is currently at 180 mg/dl and is falling.

In some embodiments, the user may press one or more of the buttons 224a, 224b, 224c, and 224d to shuffle through a number of menus or program screens that show particular status indicators, settings, and/or data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time.

The display 222 of the user interface 220 may be configured to display quick reference information when no buttons 224a, 224b, 224c, and 224d have been pressed. For example, as shown in FIG. 2, the active area of the display 222 can display the time (10:30 AM in this example), blood glucose level (118 mg/dl in this example), an indication of whether the user's blood glucose level is rising or falling (the upward arrow indicates a rising glucose level in this example, and the user's current TIL information (a 10% load in this example, which represents a normalized value of the TIL calculation as described below in connection with FIGS. 13-16B). This information can be displayed for a period of time after no button 224a, 224b, 224c, and 224d has been actuated (e.g., five seconds, 10 seconds, 30 seconds, 1 minute, 5 minutes, or the like). Thereafter, the display 222 may enter sleep mode in which the active area is blank, thereby conserving battery power. In addition or in the alternative, the active area can display particular device settings, such as the current dispensation rate or the total medicine dispensed, for a period of time after no button 224a, 224b, 224c, or 224d has been actuated (e.g., five seconds, 10 seconds, 30 seconds, 1 minute, 5 minutes, or the like). Again, thereafter the display 222 may enter sleep mode to conserve battery power. In certain embodiments, the display 222 can dim after a first period of time in which no button 224a, 224b, 224c, or 224d has been actuated (e.g., after 15 seconds or the like), and then the display 22 can enter sleep mode and become blank after a second period of time in which no button 224a, 224b, 224c, or 224d has been actuated (e.g., after 30 seconds or the like). Thus, the dimming of the display device 222 can alert a user viewing the display device 222 when the active area 223 of the display device will soon become blank.

Accordingly, when the controller device 200 is connected to the pump device 100, the user is provided with the opportunity to readily monitor infusion pump operation by simply viewing the display 222 of the controller device 200. Such monitoring capabilities may provide comfort to a user who may have urgent questions about the current operation of the pump device 100 (e.g., the user may be unable to receive immediate answers if wearing an infusion pump device having no user interface attached thereto). Moreover, the TIL information can be displayed contemporaneously with the detected blood glucose value, so the user is provided with the opportunity to make informed decisions regarding the current and future status of his or her blood glucose level.

Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 of the controller device 200 without the requirement of locating and operating a separate monitoring module.

In other embodiments, the user interface 200 is not limited to the display and buttons depicted in FIGS. 1-2. For example, in some embodiments, the user interface 220 may include only one button or may include a greater numbers of buttons, such as two buttons three buttons, four buttons, five buttons, or more. In another example, the user interface 220 of the controller device 200 may include a touch screen so that a user may select buttons defined by the active area of the touch screen display. Alternatively, the user interface 220 may comprise audio inputs or outputs so that a user can monitor the operation of the pump device 100.

Figure 3:
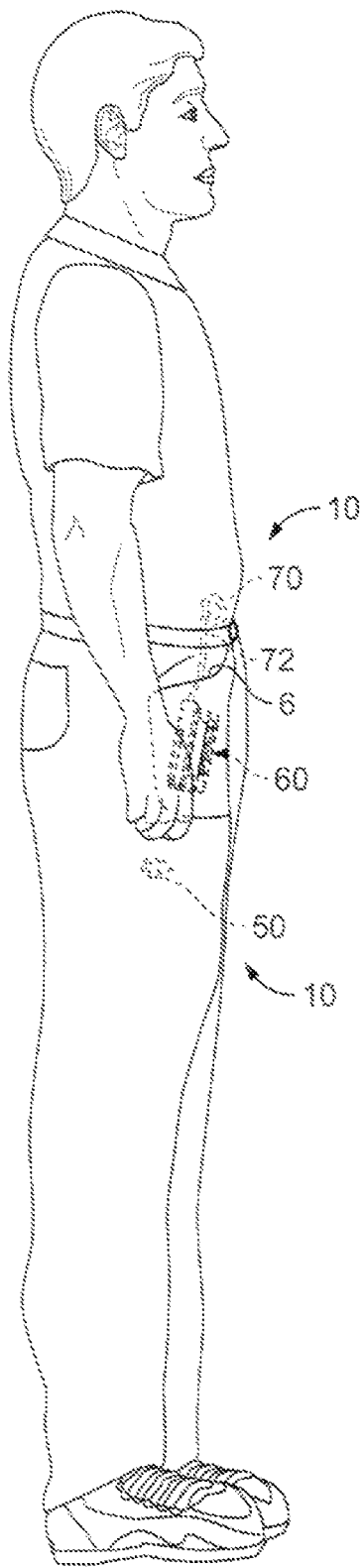
FIG. 3 is a perspective view of the infusion pump system of FIG. 1 in which the pump assembly is worn on clothing of a user, in accordance with particular embodiments.
Figure 4:
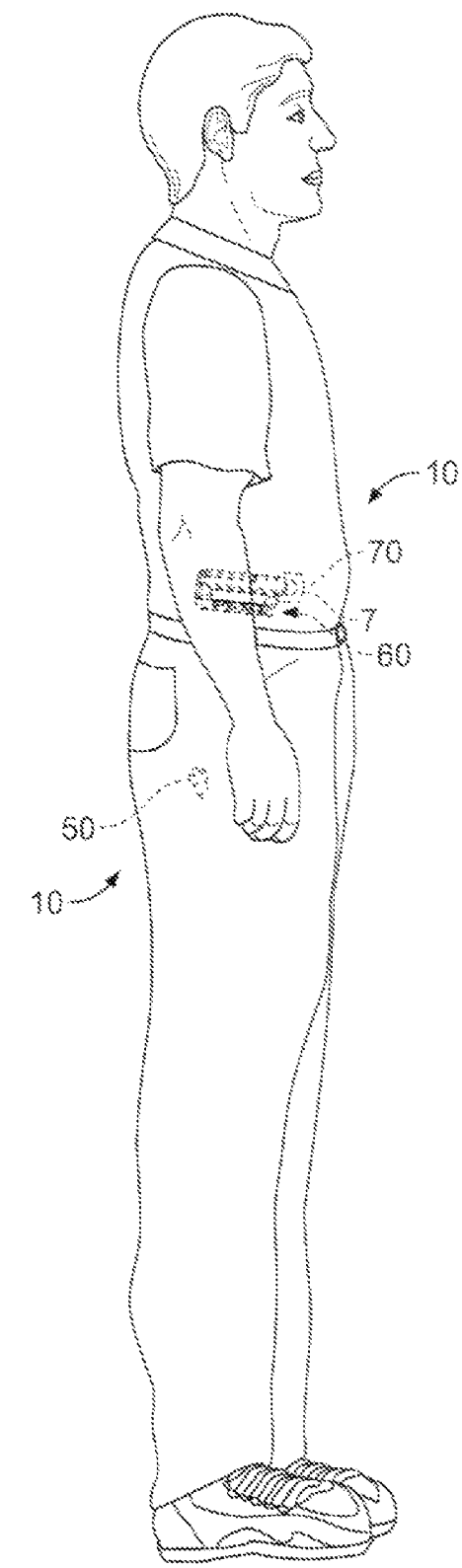
FIG. 4 is a perspective view of an infusion pump system of FIG. 1 in which the pump assembly is worn on skin of a user, in accordance with other embodiments.

Referring to FIGS. 3-4, the infusion pump system 10 may be configured to be portable and can be wearable and concealable. For example, a user can conveniently wear the infusion pump assembly 60 on the user's skin (e.g., skin adhesive) underneath the user's clothing or carry the pump assembly 60 in the user's pocket (or other portable location) while receiving the medicine dispensed from the pump device 100. The pump device 100 may be arranged in a compact manner so that the pump device 100 has a reduced length. For example, in the circumstances in which the medicine cartridge 120 has a length of about 7 cm or less, about 6 cm to about 7 cm, and about 6.4 cm in one embodiment, the overall length of the pump housing structure 110 (which contains medicine cartridge and the drive system) can be about 10 cm or less, about 7 cm to about 9 cm, and about 8.3 cm in one embodiment. In such circumstances, the controller device 200 can be figured to mate with the pump housing 110 so that, when removably attached to one another, the components define a portable infusion pump system that stores a relatively large quantity of medicine compared to the overall size of the unit. For example, in this embodiment, the infusion pump assembly 60 (including the removable controller device 200 attached to the pump device 100 having the cap 130) may have an overall length of about 11 cm or less, about 7 cm to about 10 cm, and about 9.6 cm in one embodiment; an overall height of about 6 cm or less, about 2 cm to about 5 cm, and about 4.3 cm in one embodiment; and an overall thickness of about 20 mm or less, about 8 mm to about 20 mm, and about 18.3 mm in one embodiment.

The pump system 10 is shown in FIGS. 3-4 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 may be configured to mate with the infusion set 70. In general, the infusion set 70 is tubing system that connects the infusion pump system 10 to the tissue or vasculature of the user (e.g., to deliver medicine into the user's subcutaneous tissue or vasculature). The infusion set 70 may include the flexible tube 72 that extends from the pump device 100 to the subcutaneous cannula 76 retained by a skin adhesive patch 78 that secures the subcutaneous cannula 76 to the infusion site. The skin adhesive patch 78 can retain the infusion cannula 76 in fluid communication with the tissue or vasculature of the patient so that the medicine dispensed through the tube 72 passes through the cannula 76 and into the user's body. The cap device 130 may provide fluid communication between the output end 122 (FIG. 2) of the medicine cartridge 120 and the tube 72 of the infusion set 70. For example, the tube 72 may be directly connected to the output port 139 (FIG. 2) of the cap device 130. In another example, the infusion set 70 may include a connector (e.g., a Luer connector or the like) attached to the tube 72, and the connector can then mate with the cap device 130 to provide the fluid communication to the tube 72. In these examples, the user can carry the portable infusion pump assembly 60 (e.g., in the user's pocket, connected to a belt clip, adhered to the user's skin, or the like) while the tube 72 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module.

Referring to FIG. 3, in some embodiments, the infusion pump assembly 60 is pocket-sized so that the pump device 100 and controller device 200 can be worn in the user's pocket 6 or in another portion of the user's clothing. For example, the pump device 100 and the controller device 200 can be attached together and form the assembly 60 that comfortably fits into a user's pocket 6. The user can carry the portable infusion pump assembly 60 and use the tube 72 of the infusion set 70 to direct the dispensed medicine to the desired infusion site. In some circumstances, the user may desire to wear the pump assembly 60 in a more discrete manner. Accordingly, the user may pass the tube 72 from the pocket 6, under the user's clothing, and to the infusion site where the adhesive patch 78 is positioned. As such, the pump system 10 can be used to deliver medicine to the tissues or vasculature of the user in a portable, concealable, and discrete manner. Furthermore, the monitoring device 50 can be worn on the user's skin while the pump assembly 60 is carried by the user (e.g., in a pocket). As such, the monitoring device 50 can communicate information indicative of the user's blood glucose level to the pump assembly 60 while the pump assembly 60 is used to deliver medicine through the infusion set 70. In this embodiment, the monitoring device 50 may be arranged on the user's skin at a location that is spaced apart from the infusion set 70.

Referring to FIG. 4, in other embodiments, the infusion pump assembly 60 may be configured to adhere to the user's skin 7 directly at the location in which the skin is penetrated for medicine infusion. For example, a rear surface of the pump device 100 may include a skin adhesive patch so that the pump device 100 is physically adhered to the skin of the user at a particular location. In these embodiments, the cap device 130 may have a configuration in which medicine passes directly from the cap device 130 into an infusion cannula 76 that is penetrated into the user's skin. In one example, the fluid output port 139 through the cap device 130 can include a curve or a 90° corner so that the medicine flow path extends longitudinally out of the medicine cartridge and thereafter laterally toward the patient's skin 7. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 200 that is removably attached thereto. In another example, the user can temporarily detach the controller device 200 (while the pump device 100 remains adhered to the skin 7) so as to view and interact with the user interface 220. Furthermore, the monitoring device 50 can be worn on the user's skin while the pump assembly 60 is worn on the user's skin in a different location from that where the monitoring device is worn. As such, the monitoring device 50 can communicate information indicative of the user's blood glucose level to the pump assembly 60 while the pump assembly 60 is used to deliver medicine through the infusion set 70. In this embodiment, the monitoring device 50 may be arranged on the user's skin at a location that is spaced apart from the infusion set 70.

In the embodiments depicted in FIGS. 3-4, the monitoring device 50 adheres to the user's skin 7 at the location in which the skin is penetrated by the sensor shaft 56 (to detect blood glucose levels). The sensor shaft 56 (refer to FIG. 1) penetrates the skin surface for the purpose of exposing the tip portion of the sensor shaft 56 to the tissue or the vasculature of the user. The sensor shaft 56 can detect information indicative of the user's blood glucose level and transfer this information to a circuit that is connected to the communications device 54 located within the monitoring device 50. The communication device 54 can be in wireless communication with the communication device 247 (described in connection with FIG. 9) included in the controller device 200 of the pump assembly 60.

Referring now to FIGS. 5-8, in some embodiments, the infusion pump assembly 60 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 may be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, in some embodiments, the medicine cartridge 120 containing insulin may have an expected usage life about 7 days after the cartridge is removed from a refrigerated state and the septum 121 (FIG. 2) is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin may become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some embodiments, the controller device 200 may be designed to have an expected operational life of about 1 year to about 7 years, about 2 years to about 6 years, or about 3 years to about 5 years—depending on a number of factors including the usage conditions for the individual user. Accordingly, the user is permitted to reuse the controller device 200 (which may include complex or valuable electronics) while disposing of the relatively low-cost pump device 100 after each use. Such a pump system 10 can provide enhanced user safety as a new pump device 100' (and drive system therein) is employed with each new fluid cartridge 120.

Referring to FIGS. 5-6, the pump device 100 can be readily removed from the controller device 200 when the medicine cartridge 120 is exhausted. As previously described, the medicine cartridge 120 is arranged in the cavity 116 (FIG. 2) of the pump housing 110 where it is retained by the cap device 130. In some embodiments, a portion of the pump housing 110 can comprise a transparent or translucent material so that at least a portion of the medicine cartridge 120 is viewable therethrough. For example, the user may want to visually inspect the medicine cartridge when the plunger 125 is approaching the output end 122 of the medicine cartridge, thereby providing a visual indication that the medicine cartridge may be emptied in the near future. In this embodiment, the barrel 111 of the pump housing 110 comprises a generally transparent polymer material so that the user can view the medicine cartridge 120 to determine if the plunger 125 is nearing the end of its travel length.

As shown in FIG. 5, the pump device 100 has been used to a point at which the medicine cartridge 120 is exhausted. The plunger 125 has been advanced, toward the left in FIG. 5, over a period of time so that all or most of the medicine has been dispensed from the cartridge 120. In some embodiments, the controller device 200 may provide a visual or audible alert when this occurs so as to remind the user that a new medicine cartridge is needed. In addition or in the alternative, the user may visually inspect the medicine cartridge 120 through the barrel 111 of the pump housing 110 to determine if the medicine cartridge 120 is almost empty. When the user determines that a new medicine cartridge 120 should be employed, the pump device 100 can be readily separated from the controller device 200 by actuating a release member 215. In this embodiment, the release member 215 is a latch on the controller device 200 that is biased toward a locking position to engage the pump device 100. The latch may be arranged to engage one or more features on a lateral side of the pump housing 110. As such, the user may actuate the release member 215 by moving the release member 215 in a lateral direction 216 (FIG. 5) away from the pump device 100 (e.g., by applying a force with the user's finger).

As shown in FIG. 6, when the release member 215 is actuated and moved to a position away from the pump device 100, a segmented guide rail 114a-b is free to slide longitudinally in a guide channel 214a-b without interference from the release member 215. Accordingly, the user can move the pump device 100 in a longitudinal direction 217 away from the controller device 200. For example, the segmented guide rail 114a-b may slide along the guide channel 214a-b, the extension 113 (FIG. 2) may be withdrawn from the mating depression 213 (FIG. 6), and the electrical connector 118 can be separated from the mating connector 218. In these circumstances, the pump device 100 is physically and electrically disconnected from the controller device 200 while the pump device retains the exhausted medicine cartridge 120. It should be understood that, in other embodiments, other features or connector devices can be used to facilitate the side-by-side mounting arrangement. These other features or connector devices may include, for example, magnetic attachment devices, mating tongues and grooves, or the like.

In some embodiments, the gasket 140 compressed between the pump device 100 and the controller device 200 may comprise a resilient material. In such circumstances, the gasket 140 can provide a spring-action that urges the pump device 100 to shift a small amount away from the controller device 200 when the release member 215 is moved to the unlocked position (e.g., moved in the lateral direction 216 in the embodiment shown in FIG. 5). Accordingly, in some embodiments, the pump device 100 can automatically and sharply move a small distance (e.g., about 0.5 mm to about 5 mm) away from the controller device 200 when the release member 215 is moved to the unlocked position. Such an automatic separation provides a convenient start for the user to detach the pump device 100 away from the controller device 200. Furthermore, this automatic separation caused by the spring-action of the gasket 140 can provide a swift disconnect between the electrical connectors 118 and 218 when the pump device 100 is being replaced.

Figure 7:
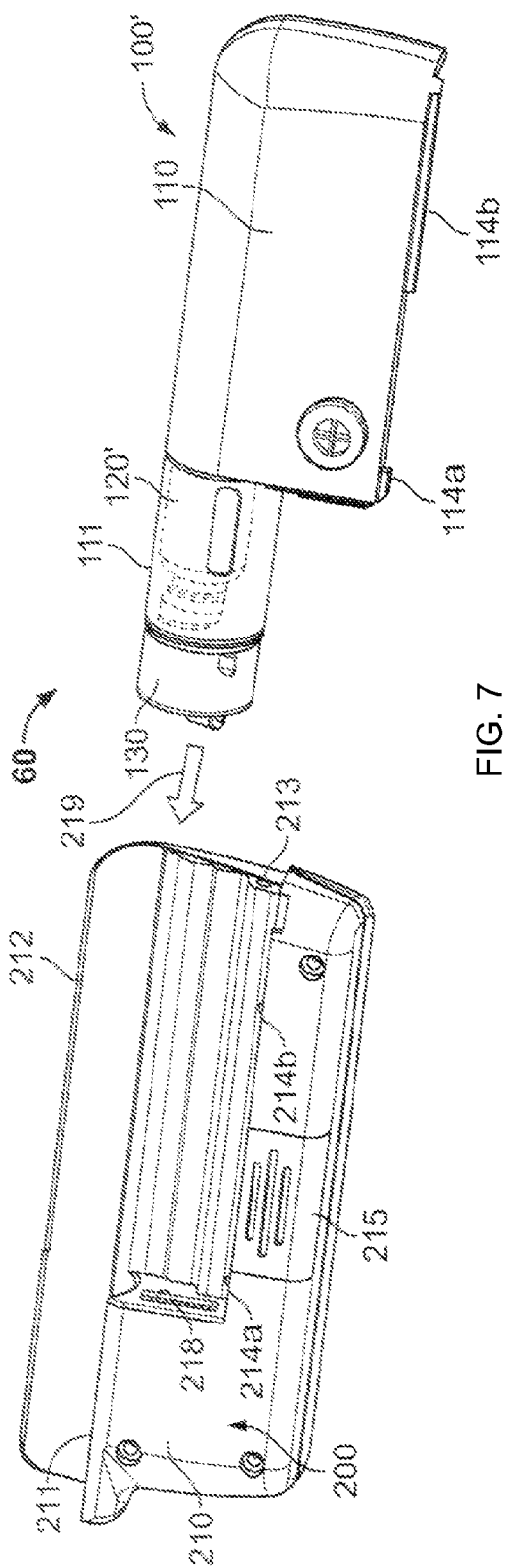
FIGS. 7-8 are perspective views of the pump device of FIGS. 5-6 being discarded and the controller device of FIGS. 5-6 being reused with a new pump device.
Figure 8:
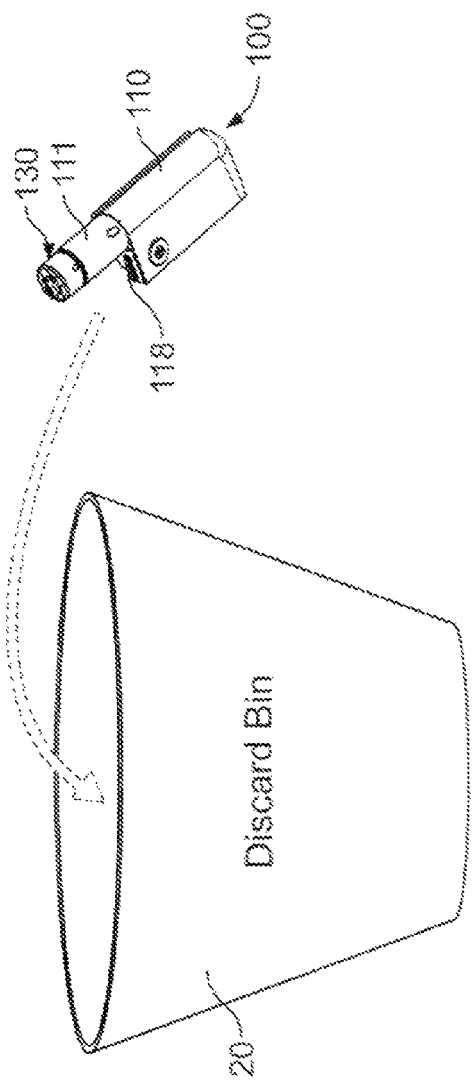

Referring to FIGS. 7-8, the same controller device 200 can be reused with a new pump device 100' having a new medicine cartridge 120' retained therein, and the previously used pump device 100 can be discarded with the exhausted medicine cartridge 120. The new pump device 100' (FIG. 7) can have a similar appearance, form factor, and operation as the previously used pump device 100 (FIGS. 5-6), and thus the new pump device 100' can be readily attached to the controller device 200 for controlled dispensation of medicine from the new medicine cartridge 120'. In some embodiments, the user may prepare the new pump device 100' for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 2). Although the tubing 72 of the infusion set 70 is not shown in FIG. 7, it should be understood that the tubing 72 may be attached to the cap device 130 prior to the cap device 130 being joined with the housing 110. For example, a new infusion set 70 can be connected to the cap device 130 so that the tubing 72 can be primed (e.g., a selected function of the pump device 100 controlled by the controller device 200) before attaching the infusion set patch to the user's skin. As shown in FIG. 7, the new medicine cartridge 120' may be filled with medicine such that the plunger 125 is not viewable through the barrel 111. In some embodiments, the user can removably attach the pump device 100 to the controller device 200 by moving the pump device 100 in a longitudinal direction 219 toward the controller device 200 such that the segmented guide rail 114a-b engages and slides within the guide channel 214a-b. When the electrical connectors 118 and 218 mate with one another, the release member 215 can engage the segmented guide rails 114a-b to retain the pump device 100 with the controller device 200.

As shown in FIG. 8, the previously used pump device 100 that was separated from the controller device (as described in connection with FIGS. 5-6) may be discarded after a single use. In these circumstances, the pump device 100 may be configured as a disposable "one-time-use" device that is discarded by the user after the medicine cartridge 120 is emptied, is expired, has ended its useful life, or is otherwise exhausted. For example, the pump device 100 may be discarded into a bin 30, which may include a trash bin or a bin specifically designated for discarded medical products. Thus, the user is permitted to dispose of the relatively low-cost pump device 100 after each use while reusing the controller device 200 (which may include complex or valuable electronics) with subsequent new pumps 100'. Also, in some circumstances, the infusion set 70 (not shown in FIG. 8, refer to FIG. 1) that was used with the pump device 100 may be removed from the user and discarded into the bin 30 along with the pump device 100. Alternatively, the infusion set 70 can be disconnected from the previous pump device 100 and attached to the new pump device 100'. In these circumstances, the user may detach the infusion set cannula 76 and patch 78 from the skin so as to "re-prime" the tubing with medicine from the new pump device 100' to remove air pockets from the tubing. Thereafter, the infusion set cannula 76 and patch 78 can be again secured to the user's skin.

Figure 9:
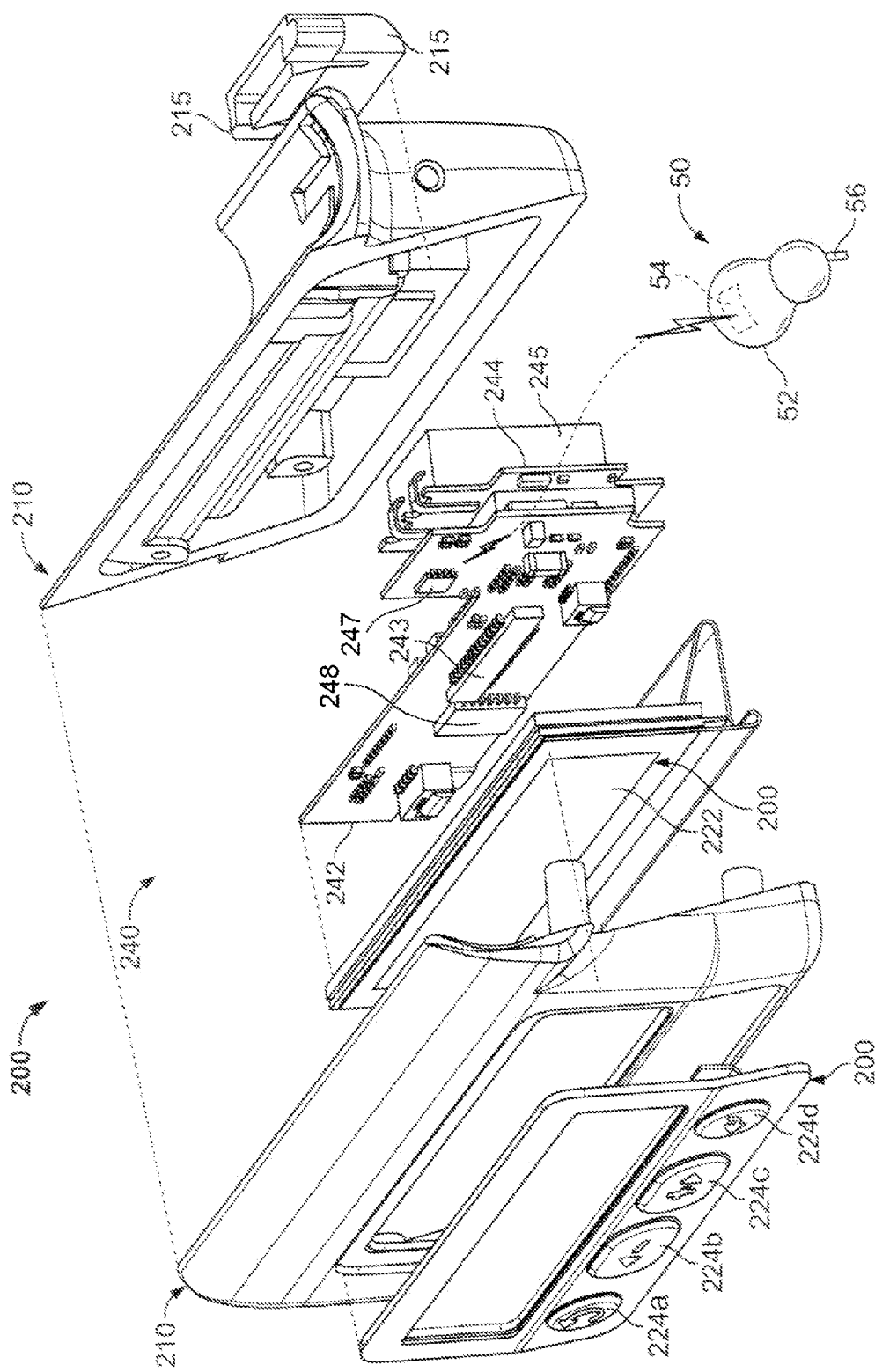
FIG. 9 is an exploded perspective view of a controller device for an infusion pump system, in accordance with some embodiments.

Referring now to FIG. 9, the controller device 200 (shown in an exploded view) houses a number of components that can be reused with a series of successive pump devices 100. In particular, the controller device 200 includes control circuitry 240 arranged in the controller housing 210 that is configured to communicate control signals to the drive system of the pump device 100. In this embodiment, the control circuitry 240 includes a main processor board 242 that is in communication with a power supply board 244. The control circuitry 240 includes at least one processor 243 that coordinates the electrical communication to and from the controller device 200 (e.g., communication between the controller device 200 and the pump device 100). The processor 243 can be arranged on the main processor board 242 along with a number of other electrical components such as memory devices (e.g., memory chip 248). It should be understood that, although the main processor board 242 is depicted as a printed circuit board, the main processor board can have other forms, including multiple boards, a flexible circuit substrate, and other configurations that permit the processor 243 to operate. The control circuitry 240 can be programmable in that the user may provide one or more instructions to adjust a number of settings for the operation of the infusion pump system 10. Such settings may be stored in the one or more memory devices, such as the memory chip 248 on the processor board 242. The control circuitry 240 may include other components, such as sensors (e.g., occlusion sensors), that are electrically connected to the main processor board 242. Furthermore, the control circuitry 240 may include one or more dedicated memory devices that store executable software instructions for the processor 243. The one or more memory devices (e.g., the memory chip 248) can also store information related to a user's blood glucose level and total insulin load (described in more detail in association with FIGS. 11-19) over a period of time.

As previously described, the controller device 200 can be electrically connected with the pump device 100 via mating connectors 118 and 218 so that the control circuitry 240 can communicate control signals to the pump device 100 and receive feedback signals from components housed in the pump device 100. In this embodiment, the electrical connector 118 (FIG. 2) on the pump device 100 is a z-axis connector, and the connector 218 (FIG. 6) on the controller device 200 is adapted to mate therewith. The electrical connector 218 on the controller device 200 is in communication with the control circuitry 240. As such, the processor 243 can operate according to software instructions stored in the memory device so as to send control signals to the pump device 100 via the connector 218.

Still referring to FIG. 9, the user interface 220 of the controller device 200 can include input components, output components, or both that are electrically connected to the control circuitry 240. For example, in this embodiment, the user interface 220 includes a display device 222 having an active area that outputs information to a user and four buttons 224a-d that receive input from the user. Here, the display 222 may be used to communicate a number of status indicators, settings, and/or menu options for the infusion pump system 10. In some embodiments, the control circuitry 240 may receive the input commands from the user's button selections and thereby cause the display device 222 to output a number of status indicators (e.g., if the pump system 10 is delivering insulin and/or if the user's blood glucose level is rising or falling), menus, and/or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the user's total insulin load, or the like). As previously described, the controller circuit 240 can be programmable in that the input commands from the button selections can cause the controller circuit 240 to change any one of a number of settings for the infusion pump system 100.

Some embodiments of the control circuitry 240 may include a cable connector (e.g., a USB connection port, another data cable port, or a data cable connection via the electrical connection 218) that is accessible on an external portion of the controller housing 210. As such, a cable may be connected to the control circuitry 240 to upload data or program settings to the controller circuit or to download data from the control circuitry 240. For example, historical data of blood glucose level, medicine delivery, and/or TIL information can be downloaded from the control circuitry 240 (via the cable connector) to a computer system of a physician or a user for purposes of analysis and program adjustments (refer, for example, to FIG. 18). Optionally, the data cable may also provide recharging power.

Figure 10:
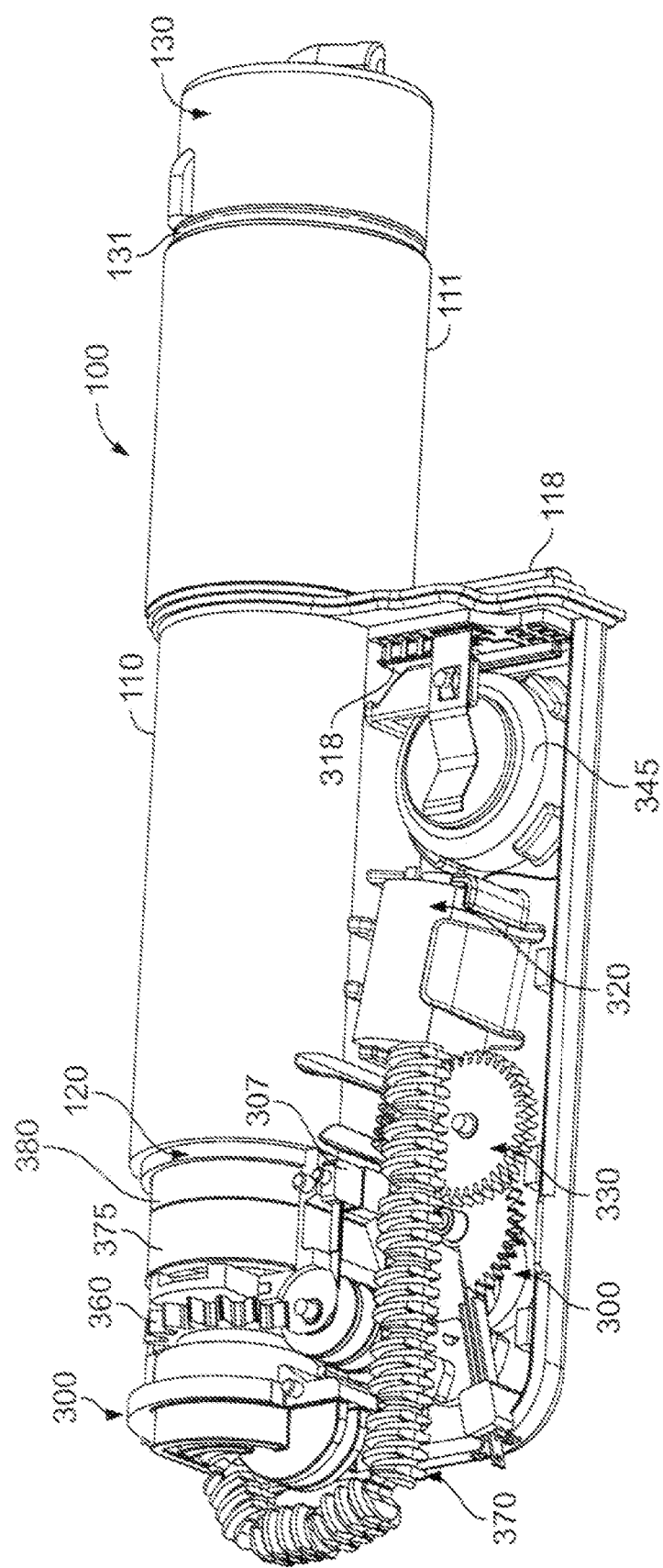
FIG. 10 is a perspective view of a portion of a pump device for an infusion pump system, in accordance with particular embodiments.

Referring to FIGS. 9-10, the control circuitry 240 of the controller device 200 may include a second power source 245 (FIG. 9) that can receive electrical energy from a first power source 345 (FIG. 10) housed in the pump device 100. In this embodiment, the second power source 245 is coupled to the power supply board 244 of the control circuitry 240. The hard-wired transmission of the electrical energy can occur through the previously described connectors 118 and 218. In such circumstances, the first power source 345 may include a high density battery that is capable of providing a relatively large amount of electrical energy for its package size, while the second power source 245 may include a high current-output battery that is capable discharging a brief current burst to power the drive system 300 of the pump device 100. Accordingly, the first battery 345 disposed in the pump device 100 can be used to deliver electrical energy over time (e.g., "trickle charge") to the second battery 245 when the controller device 200 is removably attached to the pump device 100. For example, the first battery 345 may comprise a zinc-air cell battery. The zinc-air cell battery 345 may have a large volumetric energy density compared to some other battery types. Also, the zinc-air cell battery may have a long storage life, especially in those embodiments in which the battery is sealed (e.g., by a removable seal tab or the like) during storage and before activation.

The second battery 245 may include a high current-output device that is housed inside the controller housing 210. The second battery 245 can be charged over a period of time by the first battery 345 and then intermittently deliver bursts of high-current output to the drive system 300 over a brief moment of time. For example, the second battery 245 may comprise a lithium-polymer battery. The lithium-polymer battery 245 disposed in the controller device 200 may have an initial current output that is greater than the zinc-air cell battery 345 disposed in the pump device 100, but zinc-air cell battery 345 may have an energy density that is greater than the lithium-polymer battery 245. In addition, the lithium-polymer battery 245 is readily rechargeable, which permits the zinc-air battery 345 disposed in the pump device 100 to provide electrical energy to the lithium-polymer battery 245 for purposes of recharging. In alternative embodiments, it should be understood that the second power source 245 may comprise a capacitor device capable of being recharged over time and intermittently discharging a current burst to activate the drive system 105.

Accordingly, the infusion pump system 10 having two power sources 345 and 245—one arranged in the pump device 100 and another arranged in the reusable controller device 200—permits a user to continually operate the controller device 200 without having to recharge a battery via an outlet plug-in or other power cable. Because the controller device 200 can be reusable with a number of pump devices 100 (e.g., attach the new pump device 100' after the previous pump device 100 is expended and disposed), the second power source 245 in the controller device can be recharged over a period of time each time a new pump device 100 is connected thereto. Such a configuration can be advantageous in those embodiments in which the pump device 100 is configured to be a disposable, one-time-use device that attaches to a reusable controller device 200. For example, in those embodiments, the "disposable" pump devices 100 recharge the second power source 245 in the "reusable" controller device 200, thereby reducing or possibly eliminating the need for separate recharging of the controller device 200 via a power cord plugged into a wall outlet.

Referring now to FIG. 10, the pump device 100 in this embodiment includes the drive system 300 that is controlled by the removable controller device 200 (see FIG. 2). Accordingly, the drive system 300 can accurately and incrementally dispense fluid from the pump device 100 in a controlled manner. The drive system 300 may include a flexible piston rod 370 that is incrementally advanced toward the medicine cartridge 120 so as to dispense the medicine from the pump device 100. At least a portion of the drive system 300 is mounted, in this embodiment, to the pump housing 110. Some embodiments of the drive system 300 may include a battery powered actuator (e.g., reversible motor 320 or the like) that actuates a gear system 330 to reset a ratchet mechanism (e.g., including a ratchet wheel and pawl), a spring device (not shown) that provides the driving force to incrementally advance the ratchet mechanism, and a drive wheel 360 that is rotated by the ratchet mechanism to advance the flexible piston rod 370 toward the medicine cartridge 120. Connected to piston rod 370 is a pusher disc 375 for moving the plunger 125 of the medicine cartridge 120.

Some embodiments of the drive system 300 can include a pressure sensor 380 disposed between the plunger engagement device 375 and the plunger 125 for determining the pressure within the fluid path (e.g., inside the medicine cartridge 120, the infusion set 70, and the like). For example, the fluid pressure in the medicine cartridge 120 can act upon the plunger 125, which in turn can act upon the pressure sensor 380 arranged on the dry side of the plunger 125. The pressure sensor 380 may comprise a pressure transducer that is electrically connected (via one or more wires) to a gateway circuit 318 so that the sensor signals can be communicated to the controller device 200 (e.g., via the electrical connectors 118 and 218). As such, data from the pressure sensor 380 can be received by the controller device 200 for use with, for example, an occlusion detection module to determine if an occlusion exists in the medicine flow path. Alternatively, the controller device 200 may include an optical sensor system (not shown in FIGS. 9-10) to detect occlusions in the fluid path. For example, a light emitter and light sensor may each be arranged on a sensor circuit in the controller device 200 (but aligned with the pump device 100) so that the light sensor can detect the amount of light emitted by the light emitter and subsequently reflected from a component adjacent the fluid path. The reflected light level detected may be used to determine the pressure within the fluid path.

Figure 11:
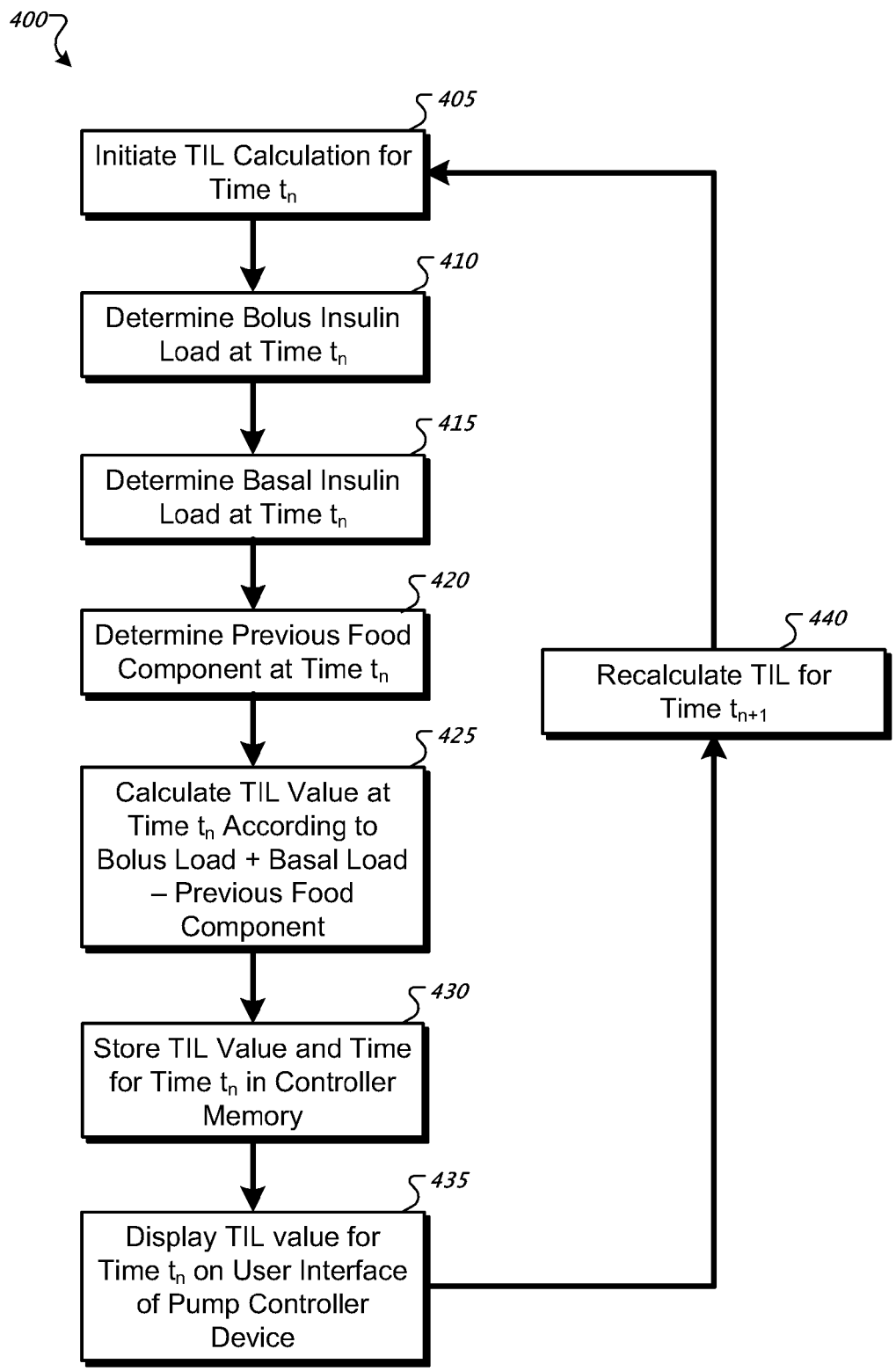
FIG. 11 is a flow diagram depicting an exemplary process used to determine a user's total insulin load (TIL), in accordance with some embodiments.

Referring now to FIG. 11, the infusion pump system 10 can be used to determine a user's TIL at a particular point in time. For example, a process 400 for determining TIL information can be implemented by the controller device 200. As previously described, the pump assembly 60 can operate to deliver insulin to the user by basal dosages, selected bolus dosages, or a combination thereof. A basal rate of insulin can be delivered in an incremental manner (e.g., dispense 0.25 U every fifteen minutes for a rate of 1.0 U per hour) to help maintain the user's blood glucose level within a targeted range during normal activity when the user is not eating or otherwise consuming food items. The user may select one or more bolus deliveries, for example, to offset the blood glucose effects caused by the intake of food or to correct for an undesirably high blood glucose level. In some circumstances, the basal rate pattern may be programmed by a health care professional during a clinical visit (or, optionally, by the user) and may remain at a substantially constant rate for a long period of time (e.g., a first basal dispensation rate for a period of hours in the morning, and a second basal dispensation rate for a period of hours in the afternoon and evening). In contrast, the bolus dosages can be dispensed in user-selected amounts based on calculations made by the controller device 200. For example, the controller device 200 can be informed of a high glucose level (e.g., by user input, data received from the glucose monitoring device 50, or the like) and can make a suggestion to the user to administer a bolus of insulin to correct for the high blood glucose reading. In another example, the user can request that the controller device 200 calculate and suggest a bolus dosage based, at least in part, on a proposed meal that the user plans to consume.

The basal and bolus insulin dispensed into the user's system may act over a period of time to control the user's blood glucose level. As such, the user's body may include some amount of insulin that has not yet acted even while the infusion pump assembly 60 is activated to deliver additional dosages (basal, bolus, or both). In these circumstances, the controller device 200 may implement a process 400 (FIG. 11) to determine the user's total insulin load (TIL), which can provide an accurate indication of the previously dispensed insulin (both basal and bolus dosages) which has not yet acted in the user's body. The TIL information can be determined in a manner that accounts for the substantial delay between the time that insulin is delivered to the tissue of the subcutaneous region and the time that this insulin reaches the blood supply. For example, the delay between a subcutaneous delivery of a bolus dosage of insulin and the peak plasma insulin level achieved from this bolus can be one hour or more. Additionally, the bolus dosage may not enter the blood stream all at once. As such, the effect of the bolus can peak at about one to two hours and then decay in a predictable manner over as much as eight hours or more (described in more detail in connection with FIG. 12). Due to the time decay effects of insulin activity, the user could be susceptible to request a subsequent bolus dosage while some insulin from a previously delivered bolus dosage has not yet acted upon the user (a scenario sometimes referred to as "bolus stacking"). To reduce the likelihood of undesirable bolus stacking, the TIL information can be determined by the controller device 200 on a periodic basis so that the user can be aware of the previously dispensed insulin which has not yet acted in the user's body. As described in more detail below, the TIL information can also be used in a bolus suggestion feature of the controller device 200 so that the suggested bolus amount accounts for the previously dispensed insulin (both basal and bolus dosages) which has not yet acted in the user's body.

For diabetics, their long term health may depend greatly on the ability to accurately control their blood glucose levels under a wide variety of conditions and to quickly and accurately respond to changes in blood glucose level from, for example, changes in activity level, carbohydrate ingestion, or the like. As such, it can be beneficial for a user to employ the infusion pump system 10 that enables the user to make well-informed decisions about future insulin boluses and basal rates. For example, the controller device 200 can readily indicate to the user his or her current TIL information, which is generally more accurate than other insulin estimation tools that are based on bolus dosages alone. Also, the controller device 200 can be used to suggest future bolus amounts based upon (1) actual and target blood glucose levels, (2) proposed food items to be consumed, and (3) the TIL information determined in a manner that accounts for both the previous bolus deliveries and the previous basal deliveries and (optionally) the user's previously consumed carbohydrates that have not yet been metabolized.

Referring in more detail to the illustrative process 400 shown in FIG. 11, the process 400 for the determining of the TIL of a user can include a number of operations performed by the controller device 200. In operation 405, the controller device 200 can initiate a TIL calculation for a particular time $t_n$ based on, for example, a request by the user (e.g., on-demand calculation) or a controller routine that determines the TIL information on a periodic basis (e.g., every 1 minute, every 2 minutes, every 5 minutes, every 10 minutes, every 30 minutes, or the like). In some embodiments, the TIL value can be calculated based on two or (optionally) three components: a bolus insulin load component, a basal insulin load component, and (optionally) a previous food component.

Figure 12:
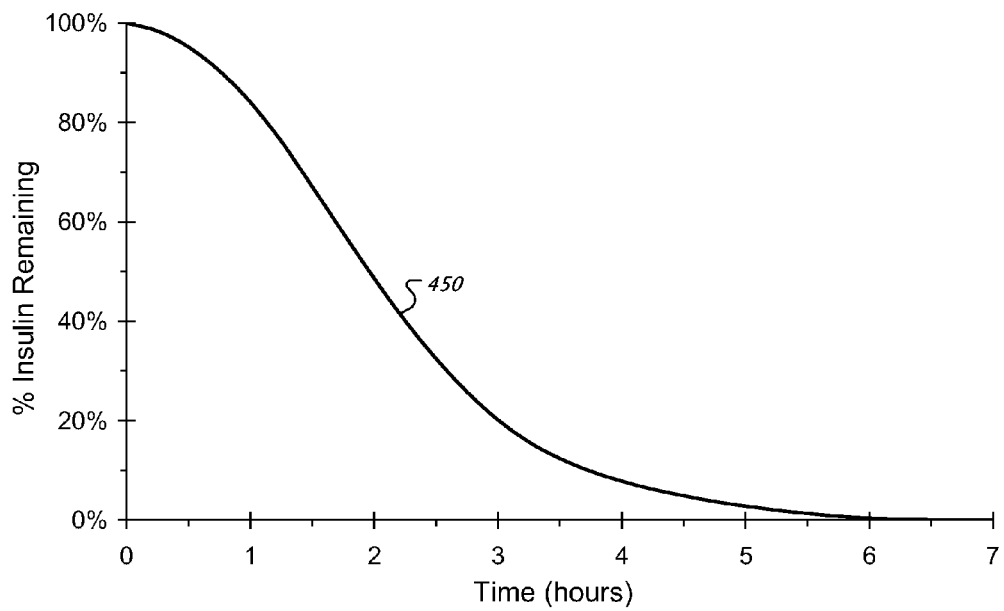
FIG. 12 is a diagram depicting an example of an insulin decay curve, which may be employed in the determination of the user's TIL in accordance with some embodiments.

In operation 410, the controller device 200 can determine the bolus insulin load at time $t_n$ based on bolus dosages that have been delivered to the patient in the recent past. In some embodiments, for each bolus dosage dispensed within a predetermined period of time before $t_n$ (e.g., 6 hours, 7 hours, 7.5 hours, 8 hours, 10 hours, or the like), the controller device 200 can estimate the amount of bolus insulin that has not yet acted in the blood stream from time-decay models generated from pharmacodynamic data of the insulin. For example, a graph of an exemplary curve depicting the percent of insulin remaining versus time can be seen in FIG. 12. In particular, FIG. 12 illustrates an example of the insulin action curve generated from pharmacodynamic data for the insulin stored in the cartridge 120. Thus, in this embodiment, the bolus insulin load component of the TIL calculation represents the sum of all recent bolus insulin dosages wherein each bolus insulin dosage is discounted by the active insulin function (which may be modeled on pharmacodynamic data as shown, for example, in FIG. 12).

Still referring to FIG. 11, in operation 415, the controller device 200 can determine the basal insulin load at time $t_n$ based on, for example, the previous basal rate during a predetermined period of time (e.g., 6 hours, 7 hours, 7.5 hours, 8 hours, 10 hours, or the like). For each basal insulin dispensation (e.g., 0.25 U dispensed every fifteen minutes, 0.5 U dispensed every fifteen minutes, 0.4 U dispensed every ten minutes, of the like), the controller device 200 can estimate the amount of basal insulin that has not yet acted in the blood stream from time-decay models generated from pharmacodynamic data of the insulin. As previously described, FIG. 12 illustrates an example of the insulin action curve generated from pharmacodynamic data for the insulin stored in the cartridge 120. Thus, in this embodiment, the basal insulin load component of the TIL calculation represents the sum of all recent basal insulin dosages wherein each basal insulin dosage is discounted by the active insulin function (which may be modeled on pharmacodynamic data as shown, for example, in FIG. 12). As described below in connection with FIG. 13, the basal insulin load at time $t_n$ may approach a constant value if the basal dosage rate remains constant over an extended period of time.

Optionally, the process 400 may include operation 420 in which the previous food component is employed in the TIL calculation. The controller device 200 can determine the previous food component based on, for example, the total carbohydrates previously entered into the controller device 200 as being consumed by the user during a predetermined period of time before $t_n$ (e.g., 6 hours, 7 hours, 7.5 hours, 8 hours, 10 hours, or the like). The previous food component can be determined, for example, by estimating the amount of carbohydrates that have been consumed but not yet metabolized by the user's body so as to effect the blood glucose level. For each of the previous food items reported by the user, the controller device 200 can estimate the previously consumed food that has not yet been metabolized from a time-based model generated from a standard glycemic index. Alternatively, when the user enter's information regarding food intake, the user can be prompted to identify the metabolization "speed" of the food item based on the glycemic index for that food. In these circumstances, the user may be prompted to input the amount of food (e.g., grams of Carbohydrate or another representative value) and then identify the glycemic index (via a numerical scale or from a list of two or more choices (e.g., "fast" metabolization and "slow" metabolization) to provide a more accurate time-based function for specific meals. When this yet-to-be-metabolized carbohydrate value is estimated, it can be treated as a "negative" insulin component in the TIL calculation by multiplying the yet-to-be-metabolized carbohydrate value by a carbohydrate ratio (e.g., 1 unit of insulin per 15 grams of carbohydrates). In some embodiments, the calculated value for the previous food component can be displayed separately to the user (e.g., to provide the user with information regarding the effects of the previously consumed carbohydrates).

Still referring to FIG. 11, in operation 425, the TIL at time $t_n$ can be calculated by summing the bolus insulin load, the basal insulin load, and (in some embodiments) the previously consumed food component, where the previous food component is treated as a negative insulin unit value. In these circumstances, the TIL values may accurately reflect both the previously dispensed insulin that has not yet acted (to reduce or otherwise effect the blood glucose level) and the previously consumed food that has not yet been metabolized (to increase or otherwise effect the blood glucose level). It should be understood from the description herein that, in alternative embodiments, the process for determining the TIL information may not include the previous food component (as described in connection with operation 420). In such embodiments, the TIL at time $t_n$ can be calculated by summing both the bolus insulin load and the basal insulin load. Because this TIL determination is not based merely on previous bolus deliveries, the TIL information may accurately reflect basal rate changes and the impact of stopping insulin delivery or changing insulin delivery (e.g., a temporary basal rate adjustment).

In operation 430, the TIL value can be stored in the memory of the controller device 200 (e.g., in the memory chip 248 or in another memory device coupled to the control circuitry 240). For example, the calculated TIL value at time $t_n$ can be stored in a database along with the time $t_n$. The database may also store the current blood glucose level at time $t_n$, which may be generated from the sensor signal received from the monitoring device 50 (FIG. 1). As described in more detail below, the database can maintain a historical record of the TIL information, the time information, and (optionally) the detected blood glucose information that is accessible by the controller device 200 or by an external computer. In addition or in the alternative, the controller device 200 can be configured to perform an on-demand calculation of the TIL value as a function of recent history by storing each input data point (e.g., basal insulin dosages, bolus insulin dosages, food intake data, etc.) and then summing each component (e.g., the basal insulin load, the bolus insulin load, and the previously consumed food component) as a function of time.

In operation 435, the TIL information can be displayed on the user interface 220 of the pump controller device 200. The TIL information can be retrieved from the memory device that stores the recently calculated TIL value. In particular embodiments, the display 222 of the user interface 220 may be configured to display a default reference information screen when the user is not activating any menu screens (e.g., a reference screen that is displayed after no buttons are pressed for a period of time). For example, as shown in FIG. 1, the display 222 can indicate the time (10:30 AM in this example), the date (January 1 in this example), the user's current blood glucose level (180 mg/dl in this example), an indication of whether the user's blood glucose level is rising or falling (the downward arrow indicates a decreasing glucose level in this example), and the recently determined TIL information (2.2 U insulin load in this example). In another example, as shown in FIG. 2, the display 222 of the user interface 220 provides a default screen that provides the time (10:30 AM in this example), the blood glucose level (118 mg/dl in this example), the indication of whether the user's blood glucose level is rising or falling (the upward arrow indicates a rising glucose level in this example), and the recently calculated TIL information (a 10% load in this example, which represents a normalized value of the TIL calculation as described below in connection with FIG. 13).

In operation 440, the process 400 can return to initiate a new TIL calculation after a period of time. For example, the operation 440 can cause the controller device 200 to calculate the TIL for time $t_{n+1}$ by returning to operation 405. As previously described, the controller device 200 can initiate the subsequent TIL calculation for the subsequent time $t_{n+1}$ based on a request from the user or based on a program that causes calculation of the TIL information on a periodic basis (e.g., every 1 minute, every 2 minutes, every 5 minutes, every 10 minutes, every 30 minutes, or the like). The subsequent TIL value for time $t_{n+1}$ can be stored in the memory of the controller device 200 (e.g., in the previously described database) and can be displayed on the user interface 220 of the controller device 200.

Referring now to FIG. 12, in some embodiments, the controller device 200 can calculate the TIL information using, at least in part, time-based models derived from pharmacodynamic data. As previously described, the TIL value of a user can include a bolus insulin load component and a basal insulin load component, each of which may be determined using a time-decay model generated from pharmacodynamic data associated with the insulin stored in the cartridge 120. As shown by way of example in FIG. 12, the controller device 200 can utilize a time-decay curve (represented by curve 450), which is generated from pharmacodynamic data, to estimate the percentage of insulin remaining in a user's body after a particular period of time.

Figure 13:
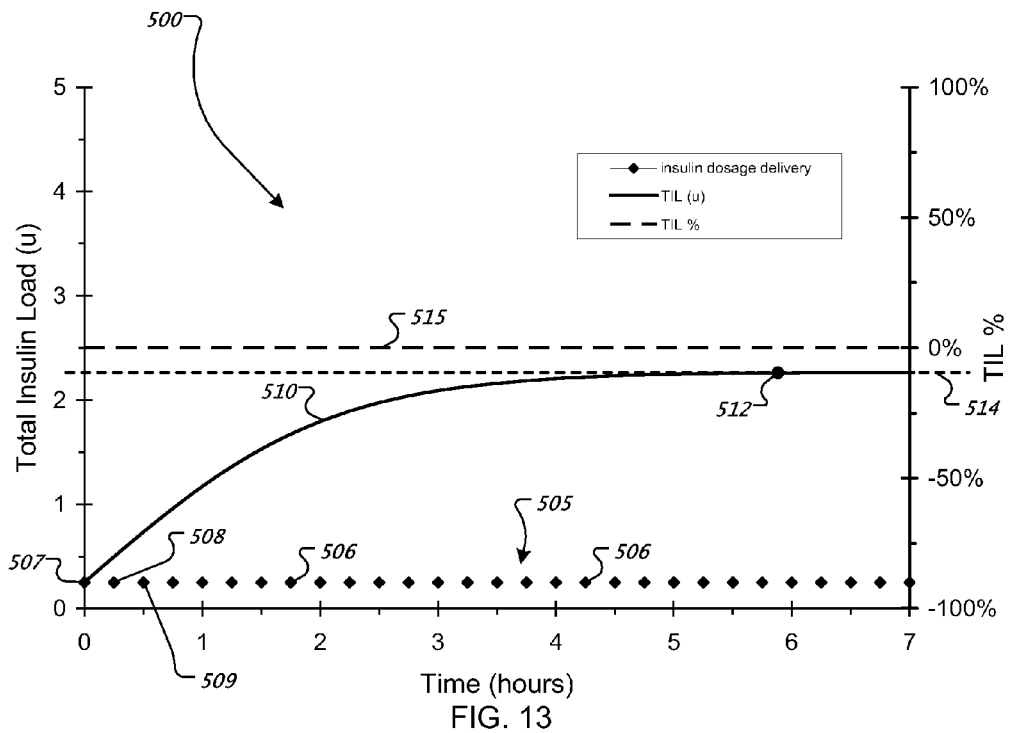
FIG. 13 is a diagram depicting an example of an insulin delivery pattern (constant basal delivery rate only) and a user's corresponding TIL and TIL % values, in accordance with some embodiments.

Referring now to FIG. 13, graph 500 is an exemplary depiction of how a constant basal delivery can affect a user's TIL information. In this example, the basal insulin deliveries are represented as a series of basal infusion points 506 (e.g., dosages of 0.25 U every fifteen minutes to provide a basal rate of 1.0 Upper hour). It should be understood from the description herein that, while the basal rate is sometimes described as a generally continuous administration, it can be implemented a series of small injections given at regular intervals. Because the basal rate is constant over a period of seven hours with no bolus dosages, the insulin delivery pattern 505 is represented as a horizontal, straight line that depicts a constant basal rate of 1.0 units/hour. For the purposes of this example, it is presumed that there were no basal or bolus insulin deliveries prior to time=0 (hours), there were no previously consumed carbohydrates acting on the user's total insulin load, and that the user's TIL (represented by TIL curve 510) was also 0.0 prior to time=0. This may occur, for example, after the user wakes in the morning and then activates the pump assembly 60 to deliver the basal insulin. As such, the user's TIL value has only a single component (basal insulin load) and is equal to zero before time=0. The other components of the TIL calculation, such as the bolus insulin load and the previous food component, are zero in this example. At time=0 the first basal infusion (represented by point 507) of 0.25 units is made. Since substantially none of the insulin delivered in the first infusion (point 507) has acted on the user at time=0, the entire contents of the infusion (0.25 units) are now part of the TIL, which is reflected in the TIL curve 510. With the subsequent boluses 508 and 509, the TIL increases, while some small portion of the previously dispensed insulin acts in the blood stream. This is estimated from a time-decay curve (refer, for example, to FIG. 12), which is generated from pharmacodynamic data. As time increases, however, the amount of insulin leaving the insulin load and entering the blood stream increases until point 512 where the amount of insulin leaving the insulin load to act in the blood stream is substantially equal to the amount of insulin entering the insulin load due to the constant basal infusion. If the basal rate remains constant, than the TIL will continue to remain at the equilibrium value shown on the graph 500. In this example, the TIL reaches equilibrium at a value of about 2.25 U (as shown on the left-side axis in graph 500).

In some circumstances, the TIL information can be stored, displayed, or both as a normalized value (e.g., the TIL % value indicated on the right-side axis of the graph 500). Although the TIL value (in units of insulin) is a useful number, that actual value can vary from user to user depending on his or her insulin intake characteristics. The TIL % value can be used as one feature to normalize the TIL calculation for convenient analysis or comparison between users. For example, the TIL % value can be calculated as follows:

TIL % value=[(Actual TIL)−(theoretical TIL$_{basal}$)]/ (theoretical TIL$_{basal}$)×100, where theoretical TIL$_{basal}$ represents the TIL that would have been generated based only on the user's basal insulin dosages (e.g., presuming no bolus insulin and no previous food components)

As such, in the example depicted in FIG. 13, the TIL % value remains at a constant of 0% (refer to TIL % curve 515) because the actual TIL value remains equal to the theoretical TIL$_{basal}$ value (based only on the user's basal insulin dosages). However, when the user receives bolus dosages and/or or has a previous food component (such circumstances are described in more detail below), the TIL % value may provide for prompt analysis of the user's insulin status and provide for easy comparison between users.

The controller device 200 can display the TIL information on the user interface 220 as the TIL value (in units of insulin as shown, for example, in FIG. 1), as the TIL % value (normalized to be a percentage as shown, for example, in FIG. 2), or as both the TIL value and the TIL % value. Moreover, the TIL information can be stored in a memory device (e.g., memory device 248) of the controller device 200 as the TIL value (in units of insulin), as the TIL % value (normalized to be a percentage), or as both the TIL value and the TIL % value.

Figure 14:
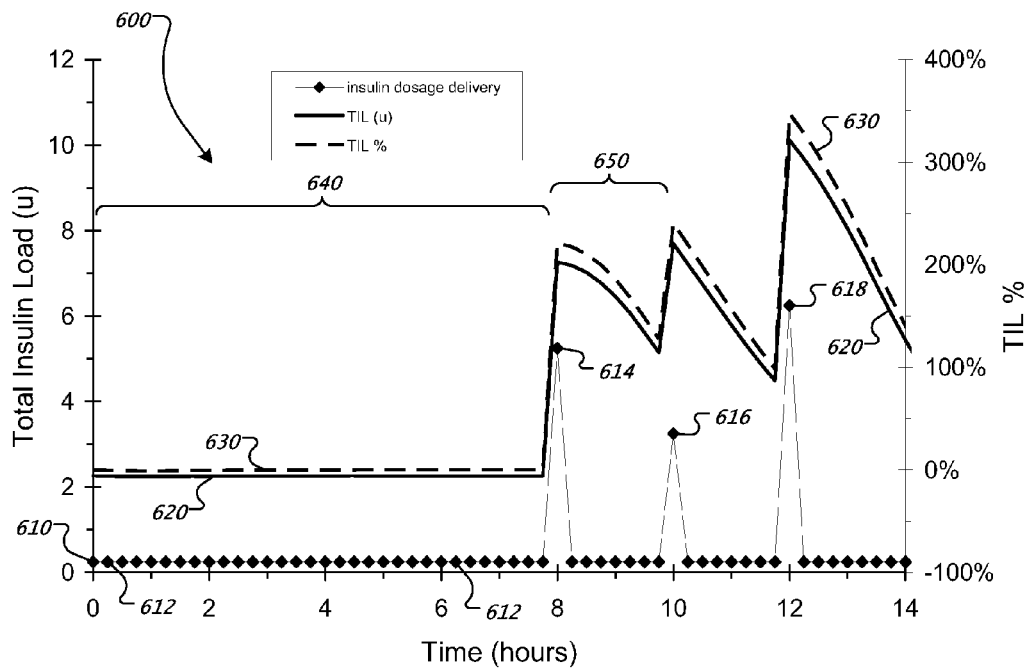
FIG. 14 is a diagram depicting an example of an insulin delivery pattern (constant basal delivery rate plus selected bolus deliveries) and a user's corresponding TIL and TIL % values, in accordance with some embodiments.

Referring now to FIG. 14, the controller device 200 can calculate the TIL information based, at least in part, on both basal insulin dispensations and bolus insulin dispensations. In this example, graph 600 includes an insulin delivery curve 610 made up of individual basal dispensations 612 and bolus dispensations 614, 616, and 618, a TIL curve 620 (which accounts for both a basal load component and a bolus load component), and a TIL % curve 630. In region 640, the basal infusion rate remains constant and no boluses are infused, so the TIL curve 620 remains at it's equilibrium value while the TIL % curve 630 remains at 0% (similar to the characteristics described in connection with FIG. 13). At about time=8 hours, a bolus delivery 614 of about 5 insulin units is delivered to the user. This bolus dosage may be selected in response to the user proposing new food intake, the user attempting to offset an elevated blood glucose level that requires correction, or the like. This bolus delivery 614 raises the user's TIL value to slightly higher than 7 units, or about 5 units plus the equilibrium value. In region 650, the user's TIL value decays or otherwise decreases as the previously dispensed insulin transitions to act in the user's blood stream (e.g., to lower or otherwise affect the user's blood glucose level). With the subsequent boluses 616 and 618, at about time=10 and time=12 hours respectively, the user's TIL value increases with each bolus, and thereafter decays.

As shown in FIG. 14, the TIL % value is also affected by the bolus deliveries 614, 616, and 618. For example, the TIL % curve 630 indicates that the TIL % value increases from 0% to about 222% immediately after the first bolus delivery 614. Although the TIL value (in units of insulin, represented in curve 620) is a useful number, that value may vary from user to user depending on his or her insulin intake characteristics (e.g., type of insulin, insulin sensitivity, carbohydrate ratio, overall insulin requirements, or the like). Here, the TIL % value of about 222% represents a normalized value for convenient analysis by the user or a health care provider. In particular, this normalized value indicates to the user that the TIL is more than two times (e.g., 222%) what it would ordinarily be if the user had maintained just the constant basal rate (from region 640) without any bolus delivery 614). In region 650, the user's TIL % value decays or otherwise decreases as the previously dispensed insulin transitions to act in the user's blood stream (e.g., to lower or otherwise affect the user's blood glucose level). With the subsequent boluses 616 and 618, at about time=10 and time=12 hours respectively, the user's TIL % value increases with each bolus, and thereafter decays.

Figure 15:
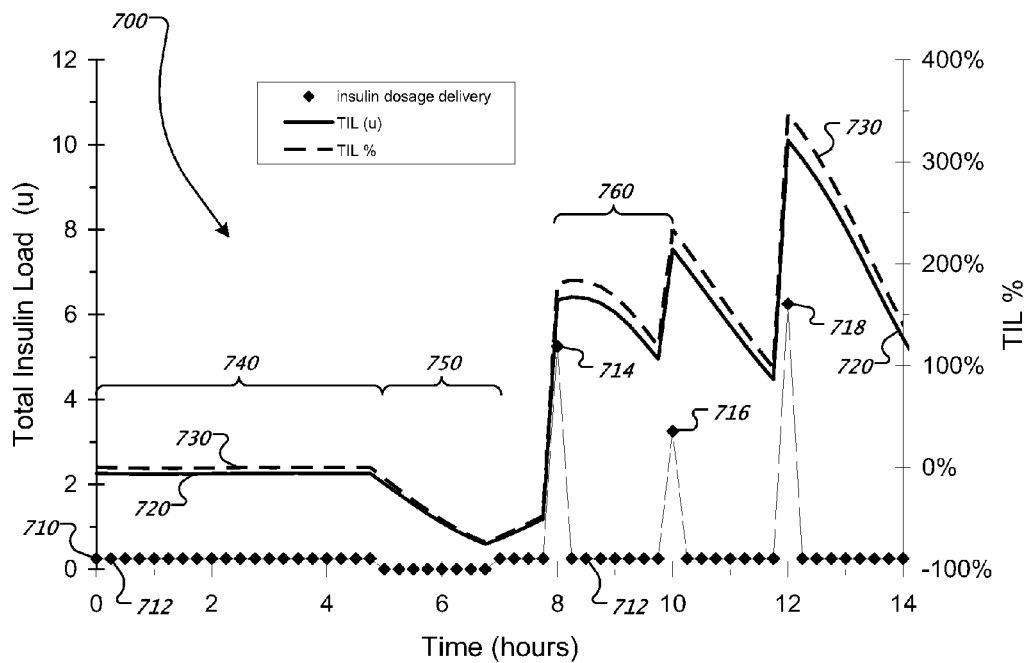
FIG. 15 is a diagram depicting an example of an insulin delivery pattern (intermittent basal delivery plus selected bolus deliveries) and corresponding TIL and TIL %, in accordance with some embodiments.

Referring now to FIG. 15, as previously described, the TIL information can be determined in a manner that accounts for both the bolus deliveries and the basal deliveries (not merely previous bolus deliveries). As such, the TIL values may accurately reflect basal rate changes and the impact of stopping insulin delivery (e.g., during periods in which insulin delivery is stopped or basal delivery is altered, during activities such as swimming or another exercise, etc.). The insulin delivery pattern in FIG. 15 is similar to the previously described scenario shown in FIG. 14, except that the basal delivery is stopped between time=5 hours and time=7 hours (refer to the basal delivery curve 710 in graph 700). For example, the graph 700 includes a region 740, in which the basal infusion rate remains constant and no boluses are infused, so the TIL curve 720 approaches a constant value while the TIL % curve 730 remains at 0% (similar to the previously described scenario shown in FIG. 14). At about time=5 hours, basal delivery is suspended for a period of approximately two hours (refer to region 750). As a result, the TIL curve 720 decays or otherwise reduces in that period of time because the previously dispensed insulin transitions to act in the user's blood stream (e.g., to lower or otherwise affect the user's blood glucose level) and no further insulin is being dispensed during that time period. Also, in the example depicted in FIG. 15, the TIL % curve 730 transitions into negative values (e.g., −25%, −50%, etc.) because the insulin dosages were ceased between time=5 hours and time=7 hours. During such periods of ceased insulin delivery, the actual TIL value may become less than theoretical TIL$_{basal}$ (e.g., the TIL that would have been generated based on the user's basal insulin dosages), which causes the TIL % values to transition into negative values. In one example, the user may readily recognize that his or her insulin load (e.g., TIL %=−25%) is approximately ¼th less than what it normally would have been if he or she had maintained the scheduled basal insulin delivery rate. Accordingly, the TIL values and the TIL % values can accurately reflect basal rate changes and the impact of stopping insulin delivery.

As shown in FIG. 15, the basal insulin rate restarts at about time=7 hours, which causes the TIL value to increase and the TIL % value to return toward 0%. In this example, a bolus delivery 714 of about 5 units is delivered to the user at about time=8 hours, thereby raising the user's TIL value about 5 units to slightly higher than 6 units. Such a bolus delivery 714 also causes the TIL % value to increase to slightly less than 200% in this example. This normalized value indicates to the user that the TIL is slightly less than two times what it would ordinarily be if the user had maintained just the constant basal rate (from region 740) without any bolus delivery 714. In region 760, the user's TIL value and the TIL % value decays or otherwise decreases as the previously dispensed insulin transitions to act in the user's blood stream (e.g., to lower or otherwise affect the user's blood glucose level). With subsequent bolus deliveries 716 and 718 at about time=10 and time=12 hours respectively, the user's TIL value and the TIL % value increases with each bolus, and thereafter decays.

Figure 16A:
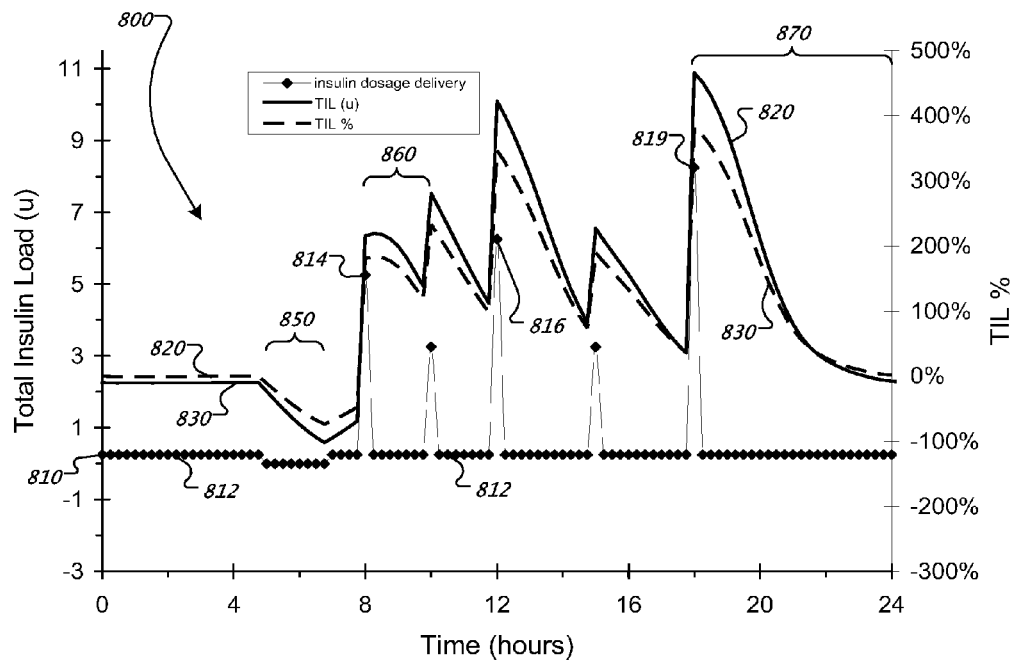
FIG. 16A is a diagram depicting an example of an insulin delivery pattern (intermittent basal delivery plus selected bolus deliveries) and a user's corresponding TIL and TIL % values, in accordance with some embodiments.

Referring now to FIG. 16A, the TIL value may return to a constant value (and the TIL % value may return to 0%) after an extended period of time with no bolus activity. For example, the graph 800 in FIG. 16A is similar to the previously described graph in FIG. 15, except that it shows the insulin delivery pattern over a greater duration of time. In some embodiments, a user may continue to receive insulin deliveries from the pump assembly 60 during his or her period of sleep. The user can receive only his or her ordinary basal dosages during this period of sleep so as to maintain his or her blood glucose level within a safe range. In the example depicted in FIG. 16A, the user receives a bolus delivery 819 before a dinner meal at about time=18 hours. Thereafter, no further bolus dosages are provided for the remainder of the day, and the user receives only the ordinary basal rate delivery (refer to region 870 in FIG. 16A). During this extended period of receiving only the basal deliveries as shown in region 870, the TIL values (refer to TIL curve 820) decay or otherwise decrease from a value greater than 10 units of insulin to a constant value of slightly greater than 2 units. Also, during this extended period in region 870, the TIL % values (refer to TIL % curve 830) decay or otherwise decrease from a normalized value of almost 400% to the constant value of 0%. Accordingly, over a period of a day or more, the TIL value and the TIL % value can "reset" or otherwise return to a constant value during periods of sleep (when the user receives nighttime basal dosages) or during other extended periods during which no bolus activity occurs.

In the previous examples, described in connection with FIGS. 14-16A, the controller device 200 calculated the TIL at any given time by summing the insulin load due to basal delivery and the insulin load due to one or more bolus deliveries (if any). These examples depict embodiments of the controller device 200 that provide the advantage of using more accurate insulin action curves to estimate the amount of insulin that has been delivered to a user (but not yet acted in that user's blood stream), and the advantage of including a basal insulin load component to the TIL calculation (thus incorporating all delivered insulin in the TIL calculation). As described previously, a calculated TIL value can be used to, for example, predict future blood glucose levels and/or can be used in the calculation of suggested bolus amounts. As such, the controller device 200 can employ the TIL information to provide accurate information to the user and to avoid "bolus stacking" and unsafe swings in blood glucose level.

In much the same way that insulin does not immediately enter the blood stream and act upon a user after subcutaneous delivery, ingested carbohydrates can also take time to fully act upon the user's blood glucose level. In some embodiments, the controller device 200 can also include a component in the TIL calculation that takes into account food which has been previously consumed but not yet acted in the user.

Figure 16B:
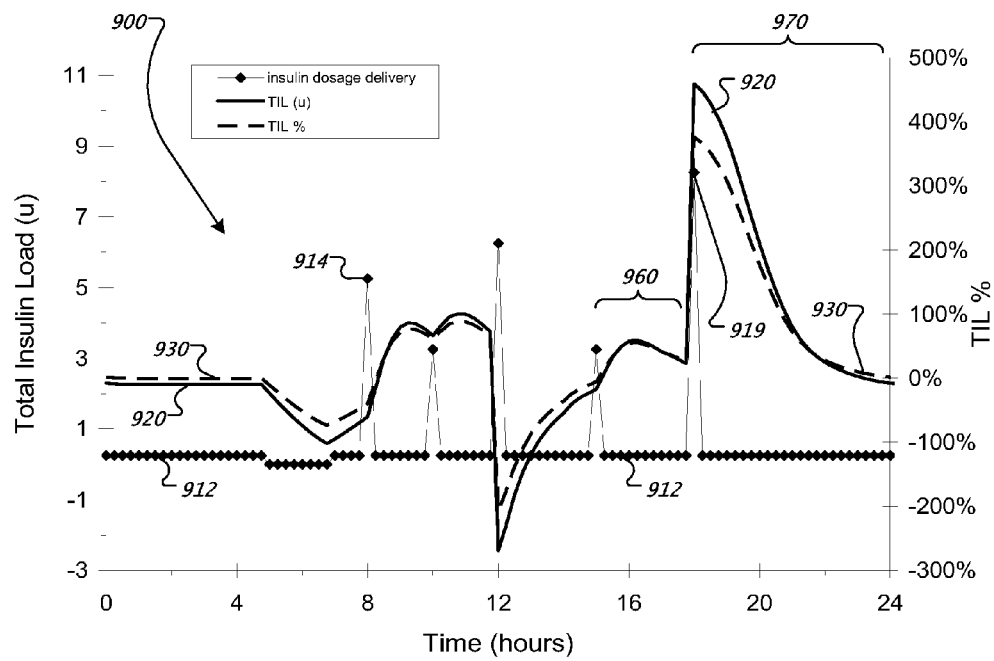
FIG. 16B is a diagram depicting an example of insulin delivery pattern (intermittent basal delivery plus selected bolus deliveries) and a user's corresponding TIL and TIL % values that account for a previously consumed food component, in accordance with some embodiments.

Referring now to FIG. 16B, as previously described, the TIL information can account for the user's previously consumed food in addition to the bolus deliveries and the basal deliveries. In these circumstances, the TIL values may accurately reflect both the previously dispensed insulin that has not yet acted and the previously consumed food that has not yet been metabolized. The insulin delivery pattern in FIG. 16B is similar to the previously described scenario shown in FIG. 16A, except that the user in FIG. 16B skips a bolus delivery at time=12 hours (note that FIG. 16A shows a bolus delivery 816 at time=12 hours). Also, in the example depicted in FIG. 16, the TIL calculation process also accounts for previously consumed food (e.g., the previous food component). For example, the graph 900 in FIG. 16B includes a basal delivery curve 910 made up of individual basal infusions 912, a TIL curve 920, and a TIL % curve 930. At about time=12 hours, the user enters meal data into the controller device 200, but no bolus delivery is dispensed (e.g., due to user error or another reason), leading to an immediate drop in the TIL curve 920 and the TIL % curve 930. This substantial decrease in the TIL value and the TIL % value is due to the fact that the process for calculating the TIL information accounts for the user's previously consumed food intake (in addition to the bolus deliveries and the basal deliveries). Thus, the controller device 200 receives information at time=12 hours that the user has consumed food but no bolus delivery was provided (e.g., a "missed bolus" situation). As such, the previous food component of the TIL calculation becomes much more significant than the bolus load component and the basal load component (thereby driving the TIL value and the TIL % value into the negative value range). In some embodiments, this drop of the TIL curve 920 into the negative region could result in the controller device 200 alerting the user to a potentially unsafe condition (e.g., a significant rise in blood glucose level) long before the user's blood glucose level begins to rise outside of a targeted range. Such a safety feature can provide enhanced protection for the user, who would have the opportunity to select a correction bolus before the blood glucose level increased to unsafe conditions.

Still referring to FIG. 16B, at about time=18 hours, a bolus delivery 915 is provided to the user, but no meal data is entered into the controller device 200. Unlike the previous situation at time=12 hours in which the user missed a bolus dosage, this may represent a "missed meal" situation at time=18 hours. This situation may occur, for example, where the user intends to eat a meal and schedules a bolus dosage, but then forgets or fails to consume the proposed meal. Such conditions can lead to a sharp increase in the TIL curve 920 and the TIL % curve 930. As such, the bolus load component of the TIL calculation becomes much more significant than the previous food component (thereby driving the TIL value and the TIL % value upward into the higher value range). In some embodiments, this sharp increase of the TIL curve 920 could result in the controller device 200 alerting the user to a potentially unsafe condition (e.g., a significant drop in blood glucose level) long before the user's blood glucose level begins to fall outside of a targeted range. Such a safety feature can provide enhanced protection for the user, who would have the opportunity to consume food items and enter the food data in the controller device 300 before the glucose level decreased to unsafe conditions. If the user did consume food at about time=18 hours but merely forgot to enter the information into the controller device 200, the user would have the opportunity to enter the meal information, thus causing the next TIL calculation to be corrected. For example, in response to the alert from the controller device 200, the controller device may prompt the user to enter the previous food information (if he or she forgot to enter the meal information) or to start the consumption of food items.

Similar to embodiments previously described in connection with FIG. 16A, the TIL value may return to a constant value (and the TIL % value may return to 0%) after an extended period of time with no bolus activity and no food consumption activity. In this example shown in FIG. 16B, during the period between time=18 hours and time=24 hours, the user may cease bolus activity and food consumption (e.g., as he or she prepares for sleep and begins to sleep overnight). During this extended period of receiving only the basal deliveries as shown in region 970, the TIL values (refer to TIL curve 920) decay or otherwise decrease to a constant value of slightly greater than 2 units. Also, during this extended period in region 970, the TIL % value (refer to TIL % curve 930) decay or otherwise decrease to a constant value of 0%.

Figure 17:
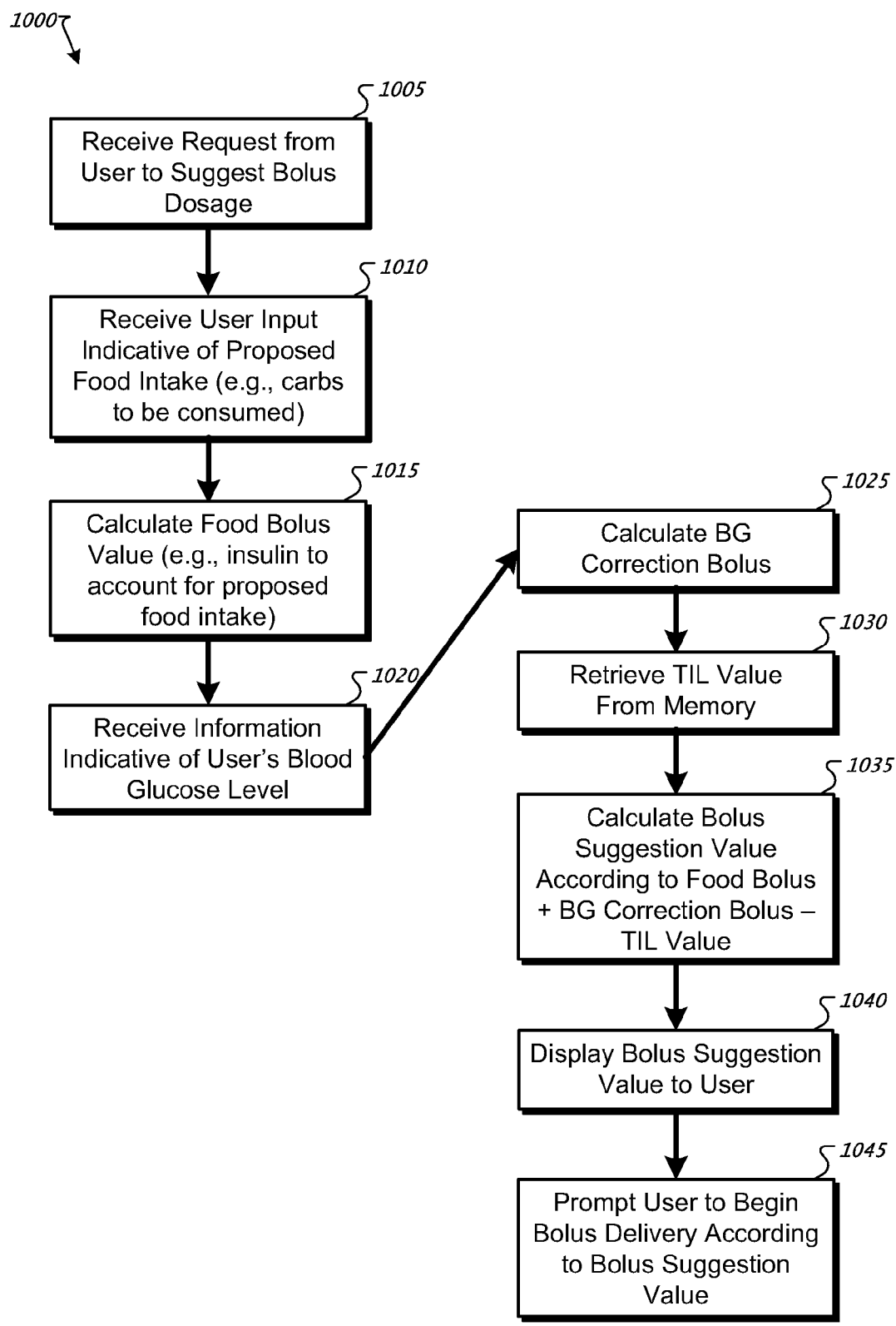
FIG. 17 is a flow diagram depicting an exemplary process used to determine a bolus suggestion, in accordance with some embodiments.

Referring now to FIG. 17, some embodiments of a process 1000 for the calculation of a suggested bolus amount can include a number of operations performed by the controller device 200 in response to user input. For example, when the user intends to consume a meal, the user can select a bolus insulin delivery to offset the blood glucose effects caused by the carbohydrates consumed with the meal. In another example, a user's blood glucose may be significantly higher than a targeted level, so the controller device 200 can suggest a correction bolus amount that will lower the blood glucose level into an acceptable range. As described in connection with FIG. 17, the controller device 200 can also take into account the user's TIL information when calculating the suggested bolus amount to the user.

In operation 1005, the controller device 200 can receive a request to suggest a bolus dosage. An exemplary request can come from the user that interacts with the user interface 220 of the controller device 200. For example, the user may request a suggested insulin bolus amount during preparation for a proposed meal. As described below, the suggested bolus value can be calculated from at least three components: a food bolus value (to offset the blood glucose effects caused by the proposed meal), a correction bolus value (to reduce the current blood glucose level into an acceptable range), and the TIL value (as previously described in connection with FIG. 11).

In operation 1010, the controller device 200 can receive input from the user indicating the amount of food to consumed. For example, the user can enter the amount and type of food that is to be consumed and the controller device 200 can determine the amount of carbohydrates contained in the food to be consumed. In another example, the user can determine the amount of carbohydrates in a proposed meal and enter this value into the controller device 200 (e.g., grams of carbohydrates or the like). In operation 1015, the controller device 200 can calculate the amount of bolus insulin to offset the proposed food intake as entered in operation 1010 (e.g., the food bolus value). For example, the number of carbohydrates determined in operation 1010 can be divided by a carbohydrate ratio (e.g., 15 grams of carbohydrates per 1 unit of insulin) to determine the dosage of bolus insulin to offset the potential blood glucose effects caused by the proposed meal.

In operation 1020, the controller device 200 can receive information indicative of the user's current blood glucose level. For example, the controller device 200 can receive information indicative of the user's blood glucose level from the glucose monitoring device 50. In another example, the user can utilize a separate blood glucose meter (e.g., a blood strip reader) and enter the results into the controller device 200. Alternatively, the glucose meter device can wirelessly communicate the blood glucose information to the controller device 200 (via communication with wireless device 247).

In operation 1025, the controller device 200 can calculate the amount of insulin (if any) to correct the current blood glucose level based on the information obtained during operation 1020. For example, the controller device 200 can subtract the user's target blood glucose level from the current level obtained during operation 1020, and then multiply this difference by an insulin sensitivity factor. Such a calculation can provide a correction bolus value that is indicative of the amount of insulin that is appropriate to reduce the current blood glucose level into an acceptable range. A positive correction bolus value indicates that the current blood glucose level is high, thereby requiring additional insulin to correct. Conversely, a negative correction bolus value indicates that the current blood glucose value is low, which will cause the suggested total bolus to be decreased.

In operation 1030, the controller device 200 can retrieve a TIL value stored in memory (previously described in connection with FIG. 11). To reduce the likelihood of undesirable bolus stacking, the TIL information can be determined by the controller device 200 on a periodic basis so that the user can be aware of the previously dispensed insulin which has not yet acted in the user's body. This TIL information can be used in a bolus suggestion feature of the controller device 200 so that the suggested bolus amount accounts for the previously dispensed insulin (both basal and bolus dosages) which has not yet acted in the user's body and (optionally) the previous food intake of the user. The TIL value can be stored in a memory device 248 (FIG. 9) of the controller device 200. As an alternative to retrieving the TIL value from the memory device, the controller device 200 can calculate a current TIL value using a process, for example, as previously described in connection with FIG. 11).

In operation 1035, the controller device 200 can calculate a suggested bolus dosage based, at least in part, on the information provided by the user. In one example, the suggest bolus dosage can be determined according to the following equation:

$$\text{Suggested Bolus Dosage} = \text{Food Bolus} + \text{Correction Bolus} - \text{TIL Value}$$

As such, the controller device 200 can provide a bolus suggestion feature that accounts for the user's TIL when suggesting a new bolus of insulin prior to a meal or other food intake. By so including the TIL information in the suggested bolus calculation, which accounts for the amount of previous basal and bolus insulin that has not yet acted in the user's body, the controller device 200 can reduce the likelihood of the user performing an unsafe level of bolus stacking. Moreover, in some embodiments, the TIL information can reflect the user's previously consumed food in addition to the bolus deliveries and the basal deliveries. Accordingly, the suggested bolus calculation, which includes the TIL information, can account for both the previously dispensed insulin that has not yet acted and the previously consumed food that has not yet been metabolized.

In operation 1040, the controller device 200 can inform the user (e.g., through display device 200, through an audio output, or through another component of the user interface) of the bolus suggestion. In one example, the display device 222 can communicate the suggested bolus amount to the user so that the user can manually input the suggested bolus value into a bolus scheduling module of controller device 200 (e.g., a separate menu option). Alternatively, as indicated in operation 1045, the controller device 200 can prompt the user to begin bolus delivery according to the suggested bolus dosage. For example, the controller device 200 can display the suggested bolus value along with a prompt that asks the user to confirm the start of the suggested bolus dosage. If the user responds in the affirmative, the controller device 200 can automatically begin the infusion. If the user responds in the negative, the user can have the opportunity manually input the suggested bolus value into a bolus scheduling module of controller device 200 (e.g., a separate menu option).

Figure 18:
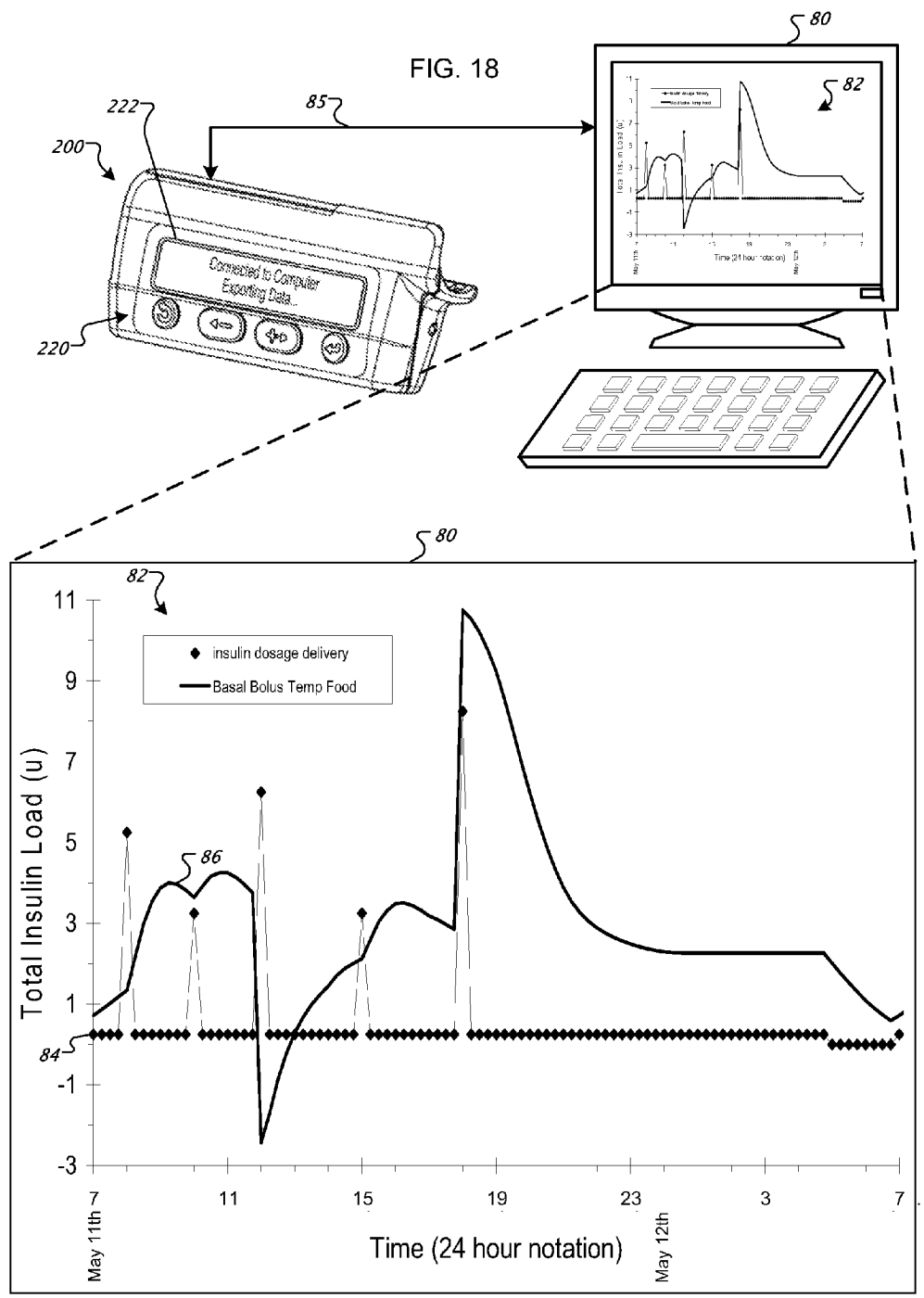
FIG. 18 is a perspective view of an infusion pump assembly connected to an external computer for displaying a plot of TIL data received from the infusion pump assembly, in accordance with some embodiments.
Figure 19:
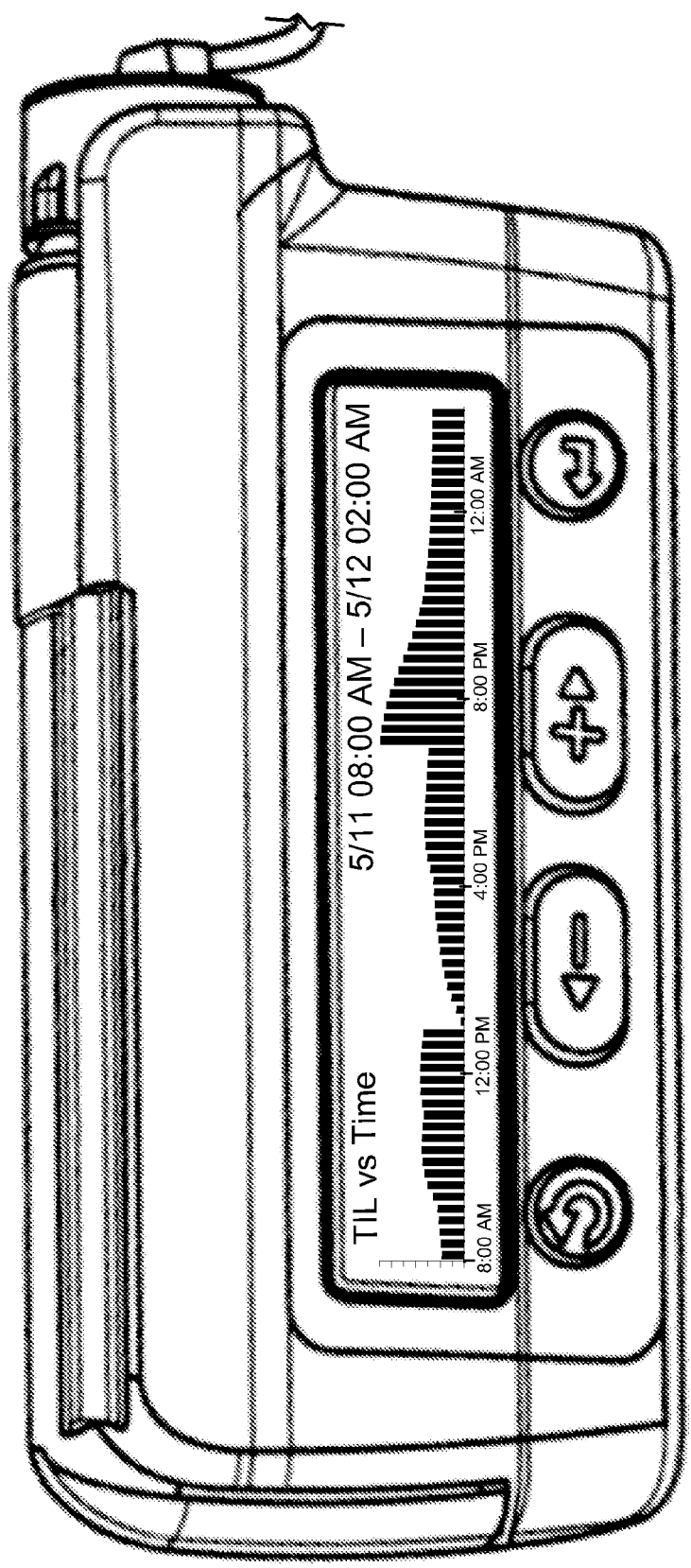
FIG. 19 is a perspective view of an infusion pump assembly displaying a plot of TIL data on a display device, in accordance with some embodiments.

Referring now to FIGS. 18-19, in some circumstances, the TIL information that is collected over a period of time can be accessed by the user or a health care provider for purposes of analysis and program adjustments. As previously described, the TIL information at time $t_n$ and the time data $t_n$ can be stored in the memory of the controller device 200. The memory of the controller device 200 may also store the detected blood glucose level at time $t_n$, which may be generated from the sensor signal received from the monitoring device 50 (FIG. 1). As such, the data stored in the controller device 200 can provide a historical record of the TIL information, the time information, and (optionally) the detected blood glucose information that is accessible by the controller device 200 or by an external computer system (e.g., a desktop computer, a laptop computer, a PDA, or the like).

For example, as shown in FIG. 18, the controller device 200 can store the TIL information and other data related to a user's blood glucose level in the memory device 248 (FIG. 9) and subsequently transfer this data to an external computer system 80 of the user or the user's health care provider. In some embodiments, the external computer system 80 can display a plot of the historical data and (optionally) execute a software program to analyze the historical data for the purposes of helping the user to better manage his or her diabetes treatment. This analysis can be used, for example, to educate the user about the benefits of entering meal information in an accurate and timely manner, to properly adjust the user's basal rate schedule, to modify user-specific parameters programmed in the controller device 200 (e.g., the carbohydrate ratio, insulin sensitivity, and the like), and to perform other management tasks.

In this illustrative example depicted in FIG. 18, the controller device 200 may communicate data to an external computer system 80 via a data connection 85. As previously described, the controller device 200 may include a cable connector (e.g., a USB connection port, another data cable port, or a data cable connection via the electrical connection 218) that is accessible on an external portion of the controller housing 210. As such, a data cable may be connected to the control circuitry 240 to export the data to the external computer system 80. Alternatively, the data connection 85 can be a wireless connection via the controller's wireless communication device 247. In such circumstances, the wireless communication device 247 can be configured to wirelessly communicate with the monitoring device 50 (FIG. 1) and with the external computer system 80 (FIG. 18). When the controller device 200 is connected to the computer system 80 via the data connection 85, the controller device 25 can execute a data exporting module in which the TIL information, the time information, the detected blood glucose information, and other treatment information is exported in a suitable format to the external computer system 80. In some circumstances, the controller device 200 may be detached from the pump device during the process of exporting data, so the controller device 200 can suspend dispensation operations (e.g., suspends basal infusion, bolus infusion, accessibility to certain menus via the user interface 220, and the like). While controller device executes the data exporting module, the controller device 200 may indicate on the display device 222 that the controller device 200 is in this mode by displaying a message such as "Exporting Data . . . " or the like.

Still referring to FIG. 18, after the data has been transferred to the computer system 80, the computer system 80 can display the TIL information and other treatment data is a usable format. For example, the display device of the computer system 80 can provide a time-based plot 82 that indicates the user's insulin delivery pattern 84 and the user's TIL information 86 with respect to time. The TIL information in the plot 82 can be display as the actual TIL value (in units of insulin), the TIL % value (normalized to be a percentage), or both. The computer system 80 may provide a time-based plot that indicates the user's detected blood glucose levels with respect to time. Optionally, this blood glucose information can be display on the same plot 82 as the TIL information 86. Thus, the external computer system 80 can display the plot 82 of the user's historical treatment data and may optionally execute a software program to analyze the historical treatment data for the purposes of helping the user to better manage his or her diabetes treatment. By presenting the TIL information and other treatment data to the user in an understandable, graphical format (such as the time-based plot 82), the health care provider is readily equipped to educate the user about the benefits of entering meal information in an accurate and timely manner, to properly adjust the user's basal rate schedule, to modify user-specific parameters programmed in the controller device 200 (e.g., the carbohydrate ratio, insulin sensitivity, and the like), and to perform other management tasks.

In another illustrative example depicted in FIG. 19, some embodiments of the controller device 200 can be configured to display the TIL information and other treatment data is a graphical format data on the local display device 222. For example, as shown in FIG. 19, the controller device 200 can access the historical treatment data stored in the memory device 248 so as to generate a graphical representation 226 of the TIL information over a period of time. In this embodiment, the TIL information is displayed on the display device in the form of a bar graph 226 that indicates the user's TIL information over a period of hours. The display device 22 can be configured to display a y-axis that is representative of the scale for the TIL value of the TIL % value. Also, the display device 222 can shows a set of time increments along an x-axis of the bar graph 226. As such, the controller device 200 can provide prompt access to the TIL information by a user or health care provider, and can readily present such information in an understandable, graphical format (such as the time-based plot 226). In doing so, the user can assess his or her insulin treatment performance over a recent period of time and make proper adjustments to his or her basal rate, bolus dosages, eating schedule, or the like. In the event that the user seeks to review the TIL information over a longer period of time, the controller device 200 can display the TIL values for this extended period (e.g., a 24-hour period) on the display device 222 by averaging the TIL values during each one hour period into a single value. In such circumstances, the hour-averaged values (e.g., 24 averaged values for a 24 hour period) can then be displayed in a graphical format, such as bar graph, that indicates the trends of the user's TIL information.

A number of embodiments of the invention have been described. Nevertheless, it will be understood that various modifications may be made without departing from the spirit and scope of the invention. Accordingly, other embodiments are within the scope of the following claims.

What is claimed is:

1. A method of operating an insulin infusion pump system, comprising:
   determining a total insulin load for a particular time that accounts for a bolus insulin load, a basal insulin load, and a previous food component, wherein: the bolus insulin load is indicative of one or more bolus insulin dosages that have been dispensed into a user from a portable infusion pump system but not yet acted in the user, the basal insulin load is indicative of one or more basal insulin dosages that have been dispensed into the user from the portable infusion pump system but not yet acted in the user; and the previous food component is based upon previous food intake that has not yet metabolized in the user;

storing a calculated value for the total insulin load and a time value for the particular time in a computer-readable memory device of the portable infusion pump system; and displaying the calculated value for the total insulin load on a display device of the portable infusion pump system.

2. The method of claim 1, wherein displaying the calculated value for the total insulin load on a display device comprises contemporaneously displaying a glucose value indicative of the blood glucose level of the user and the calculated value for the total insulin load.

3. The method of claim 1, further comprising providing plot data to at least partially define a time-based plot of calculated values for total insulin load versus time.

4. The method of claim 3, further comprising displaying the time-based plot of calculated values for total insulin load versus time on the display device of the portable infusion pump system.

5. The method of claim 3, wherein the plot data is exported to an external computer system to display the time-based plot of calculated values for total insulin load versus time on a display device of the external computer system.

6. The method of claim 1, further comprising receiving glucose information from a monitoring device, the glucose information being indicative of a detected blood glucose level of the user.

7. The method of claim 6, further comprising displaying a glucose value indicative of the detected blood glucose level of the user on the display device of the portable infusion pump system, wherein the display device contemporaneously displays the glucose value and the calculated value for the total insulin load.

8. A method of operating an insulin infusion pump system, comprising:

receiving user input indicative of a request to suggest a bolus dosage;

receiving user input indicative of a proposed food intake to be consumed by a user of a portable infusion pump system;

receiving glucose information indicative of a glucose level of the user;

storing a calculated value for a total insulin load of the user in a computer-readable memory device of the portable infusion pump system, wherein the total insulin load accounts for (i) a bolus insulin load indicative of one or more bolus insulin dosages that have been dispensed into the user but not yet acted in the user, (ii) a basal insulin load indicative of one or more basal insulin dosages that have been dispensed into the user from the portable infusion pump system but not yet acted in the user; and (iii) a previous food component based upon previous food intake that has not yet metabolized in the user;

determining a bolus suggestion value according to a function that includes the total insulin load of the user; and displaying the bolus suggestion value on a display device of the portable infusion pump system.

9. The method of claim 8, wherein further comprising prompting the user initiate a bolus dosage in the amount of the suggested bolus value displayed on the display device.

10. The method of claim 8, wherein the bolus suggestion value is determined according to the function:

bolus suggestion value=(proposed food intake bolus)+ (correction bolus)−(total insulin load of the user).

11. The method of claim 10, wherein the proposed food intake bolus is determine according to: (estimated value of carbohydrates to be consumed)×(carbohydrate ratio).

12. The method of claim 10, wherein the correction bolus is determine according to: (the glucose level of the user−a target glucose level)×(an insulin sensitivity factor).

13. The method of claim 10, wherein the total insulin load of the user at time $t_n$ is determine according to: (bolus insulin load at time $t_n$)+(basal insulin load at time $t_n$)−(previous food component at time $t_n$).

14. A method of operating an insulin infusion pump system, comprising:

dispensing insulin from a portable infusion pump system to a user, the portable infusion pump system comprising a pump housing at least partially containing a pump drive system to dispense the insulin through a flow path to the user, and a controller that activates the pump drive system to dispense the insulin from the portable pump housing;

wirelessly receiving a communication from a glucose sensor device indicative of glucose information, the glucose information being indicative of a detected blood glucose level of the user;

storing a calculated value for a total insulin load and a time value for the particular time in a computer-readable memory device of the portable infusion pump system, the total insulin load being indicative of bolus and basal insulin dosages that have dispensed but not yet acted in the user; and displaying contemporaneously on a user interface display of the portable infusion pump system a glucose value indicative of the detected blood glucose level of the user and the calculated value for the total insulin load.

15. The method of claim 14, wherein the displaying step comprises contemporaneously displaying the glucose value and the calculated value for the total insulin load in a reference information screen that is displayed when the user has not activated any menu options for a particular period of time.

16. The method of claim 14, further comprising determining the total insulin load according to a function that accounts for (i) a bolus insulin load indicative of one or more bolus insulin dosages that have been dispensed into the user but not yet acted in the user, (ii) a basal insulin load indicative of one or more basal insulin dosages that have been dispensed into the user from the portable infusion pump system but not yet acted in the user; and (iii) a previous food component based upon previous food intake that has not yet metabolized in the user.

17. The method of claim 14, further comprising exporting via a data connection between the portable infusion pump system and an external computer system the calculated values for the total insulin load and the corresponding time values.

18. The method of claim 17, wherein when the controller exports the calculated values for the total insulin load and the corresponding time values to the external computer system, the external computer system displays the calculated values for the total insulin load in a time-based plot.

19. The method of claim 14, further comprising determining the total insulin load according to a function that accounts for at least (i) a bolus insulin load indicative of one or more bolus insulin dosages that have been dispensed into the user but not yet acted in the user, and (ii) a basal insulin load indicative of one or more basal insulin dosages that have been dispensed into the user from the portable infusion pump system but not yet acted in the user.

20. The method of claim 14, wherein the controller comprises a controller housing that removably attaches to the pump housing.

* * * * *